United States Patent
Mrksich et al.

(10) Patent No.: US 12,098,215 B2
(45) Date of Patent: Sep. 24, 2024

(54) FUSION PROTEIN CONSTRUCT

(71) Applicant: NORTHWESTERN UNIVERSITY, Evanston, IL (US)

(72) Inventors: Milan Mrksich, Hinsdale, IL (US); Justin A. Modica, Chicago, IL (US)

(73) Assignee: NORTHWESTERN UNIVERSITY, Evanston, IL (US)

( * ) Notice: Subject to any disclaimer, the term of this patent is extended or adjusted under 35 U.S.C. 154(b) by 1223 days.

(21) Appl. No.: 16/307,621

(22) PCT Filed: Jun. 6, 2017

(86) PCT No.: PCT/US2017/036160
§ 371 (c)(1),
(2) Date: Dec. 6, 2018

(87) PCT Pub. No.: WO2017/214151
PCT Pub. Date: Dec. 14, 2017

(65) Prior Publication Data
US 2019/0161556 A1    May 30, 2019

Related U.S. Application Data

(60) Provisional application No. 62/346,369, filed on Jun. 6, 2016.

(51) Int. Cl.
C07K 16/46 (2006.01)
A61P 19/02 (2006.01)
(Continued)

(52) U.S. Cl.
CPC ............. *C07K 16/46* (2013.01); *A61P 19/02* (2018.01); *A61P 35/00* (2018.01); *A61P 37/00* (2018.01);
(Continued)

(58) Field of Classification Search
None
See application file for complete search history.

(56) References Cited

U.S. PATENT DOCUMENTS 5,932,448 A    8/1999  Tso et al.
6,511,663 B1   1/2003  King et al.
(Continued)

FOREIGN PATENT DOCUMENTS

EP    0453082 A1    10/1991
EP    1258255 A1    11/2002
(Continued)

OTHER PUBLICATIONS

Kaltenbach et al. ChemBioChem 2011, 12, 2208-2216 (Year: 2011).*
(Continued)

*Primary Examiner* — Karl J Puttlitz
(74) *Attorney, Agent, or Firm* — MARSHALL, GERSTEIN & BORUN LLP

(57) ABSTRACT

The disclosure provides constructs comprising a first fusion protein, a second fusion protein, and a linker, wherein the first fusion protein and the second fusion protein each include an affinity reagent and a reactive enzyme, and the linker includes a first and second functional groups specific for irreversibly inhibiting the first and second fusion protein reactive enzymes. The disclosure further provides a method including (a) contacting a first fusion protein including an affinity reagent and a reactive enzyme with a linker including a functional group specific for irreversibly inhibiting the first fusion protein reactive enzyme thereby coupling the first fusion protein and the linker, and (b) contacting a second fusion protein including an affinity reagent and a reactive enzyme with the linker, the linker including a functional group specific for irreversibly inhibiting the sec-
(Continued)

ond fusion protein reactive enzyme thereby coupling the second fusion protein and the linker.

19 Claims, 5 Drawing Sheets

Specification includes a Sequence Listing.

(51) Int. Cl.
  *A61P 35/00* (2006.01)
  *A61P 37/00* (2006.01)
  *C07K 16/32* (2006.01)
  *C12N 9/18* (2006.01)
  *A61K 39/00* (2006.01)

(52) U.S. Cl.
  CPC ............... *C07K 16/32* (2013.01); *C12N 9/18* (2013.01); *C12Y 301/01074* (2013.01); *A61K 2039/505* (2013.01); *C07K 2317/24* (2013.01); *C07K 2317/55* (2013.01); *C07K 2317/565* (2013.01); *C07K 2317/73* (2013.01); *C07K 2317/92* (2013.01); *C07K 2317/94* (2013.01); *C07K 2319/00* (2013.01); *C07K 2319/61* (2013.01); *C12Y 201/01037* (2013.01); *C12Y 301/21002* (2013.01); *C12Y 302/01021* (2013.01); *C12Y 304/11018* (2013.01); *C12Y 304/24024* (2013.01); *C12Y 305/02006* (2013.01)

(56) References Cited

U.S. PATENT DOCUMENTS

| | | | |
|---|---|---|---|
| 7,429,472 | B2 | 9/2008 | Darzins et al. |
| 7,527,787 | B2 | 5/2009 | Chang et al. |
| 7,871,622 | B2 | 1/2011 | Chang et al. |
| 7,888,086 | B2 | 2/2011 | Darzins et al. |
| 7,906,121 | B2 | 3/2011 | Chang et al. |
| 2003/0167524 | A1* | 9/2003 | Rooijen ............ C12N 15/8258 800/281 |
| 2004/0115130 | A1 | 6/2004 | Johnsson et al. |
| 2005/0163782 | A1 | 7/2005 | Glaser et al. |
| 2006/0292651 | A1 | 12/2006 | Juillerat et al. |
| 2010/0075394 | A1 | 3/2010 | Johnsson et al. |
| 2010/0183516 | A1* | 7/2010 | Ribbert ............... A61K 47/545 435/375 |
| 2011/0123522 | A1 | 5/2011 | Arber |
| 2011/0201514 | A1 | 8/2011 | Johnsson et al. |
| 2015/0369816 | A1* | 12/2015 | Mrksich ............. C07F 9/65515 506/18 |
| 2016/0297820 | A1* | 10/2016 | Seow .................... A61K 47/55 |

FOREIGN PATENT DOCUMENTS

| | | |
|---|---|---|
| EP | 1900379 A2 | 3/2008 |
| EP | 2414391 A1 | 2/2012 |
| WO | WO-92/004053 A1 | 3/1992 |
| WO | WO-2006/020258 A2 | 2/2006 |

OTHER PUBLICATIONS

Hussain et al. Biomacromolecules 2013, 14, 2510-2520 (Year: 2013).*
Lemercier et al., Angew. Chem. Int. Ed. 2007, 46, 4281-4284 (Year: 2007).*
Zimmermann et al., Angew. Chem. Int. Ed. 2014, 53, 4717-4720 (Year: 2014).*
Gautier et al., J. Am. Chem. Soc. 2009, 131, 17954-17962 (Year: 2009).*
Bosch et al., Biophysical Journal, 2014, 107(4) 803-814 (Year: 2014).*
Urh et al., Current Chemical Genomics, 2012, 6, (Suppl 1-M8) 72-31 (Year: 2012).*
International Preliinary Report on Patentability and Written Opinion for International application No. PCT/US2017/036160, mailed Sep. 1, 2017.
Erhart et al., Chemical development of intracellular protein heterodimerizers, Chemistry & Biology, 20:549-557 (2013).
Hodneland et al., Selective immobilization of proteins to self-assembled monolayers presenting active site-directed capture ligands, PNAS, 99:5048-52 (2002).
Modica et al., Modular assembly of protein building blocks to create precisely defined megamolecules, ChemBioChem, 13:2331-4 (2012).
Bodor et al., Analysis of Protein Turnover by Quantitative SNAP-Based Pulse-Chase Imaging, Unit 8.8 IN: Current Protocols in Cell Biology, Jun. 2012.
Chatterjee et al., *Saccharomyces cerevisiae* THI4p is a suicide thiamine thiazole synthase, Nature, 478(7370):542-6 (2011).
Chen et al., Fusion protein linkers: property, design and functionality, Adv. Drug Deliv. Rev., 65(10):1357-69 (2013).
Gu et al., Protein tag-mediated conjugation of oligonucleotides to recombinant affinity binders for proximity ligation, New Biotechnology, 30(2):144-52 (Jan. 2013).
Haruki et al., Exploiting ligand-protein conjugates to monitor ligand-receptor interactions, PLoS One, 7(5):e37598 (2012).
Hussain et al., SNAP-tag technology mediates site specific conjugation of antibody fragments with a photosensitizer and improves target specific phototoxicity in tumor cells, Bioconjug. Chem., 22(12):2487-95 (2011).
Metcalf et al., Synthetic tuning of domain stoichiometry in nanobody-enzyme megamolecules, Bioconjugate Chem., 32(1):143-52 (Jan. 2021).
Tomoshige et al., Efficient protein knockdown of HaloTag-fused proteins using hybrid molecules consisting of IAP antagonist and HaloTag ligand, Bioorganic & Medicinal Chemistry, 24:3144-8 (2016).

* cited by examiner

FUSION PROTEIN CONSTRUCT

FIELD OF THE DISCLOSURE

The disclosure relates generally to fusion protein constructs and their methods of preparation and use. More particularly, the disclosure relates to precisely-defined fusion protein constructs comprising at least a first fusion protein and a second fusion protein coupled by a linker, prepared by a modular synthesis.

BACKGROUND

Biologic drugs, specifically monoclonal antibodies (mAbs) and those that incorporate antibody fragments are of interest in the pharmaceutical industry due to their ability to specifically target disease-related proteins in circulation or on cell surfaces. Next-generation antibody therapeutics, those that show enhanced therapeutic potential, have been created by increasing the antibody valency, attaching effector molecules that increase cytotoxicity and half-life, and by using formats that direct the immune system toward clearing targets. These molecules, however, are often challenging to produce in high-yield and with synthetic flexibility that permits a desired function to be systematically optimized.

For example, current antibody formats with expanded functionality must be arduously optimized for stability or function as they feature multiple domains that must be expressed concurrently. Current chemical methods require the engineering of a reactive amino acid or the use of a preexisting reactive amino acid side chain to attach payloads to the antibody scaffold. In many cases, products of these reactions yield heterogeneous populations of products. Such direct amino-acid modifications may also not be stable or cause deleterious effects to the pharmacological properties of the parent molecule (e.g. increased hydrophobicity, aggregation, immunogenicity, etc.) therefore a great deal of effort must be directed toward choosing a suitable location for attaching the payload.

Additionally, current antibody technologies do not enable the product of scaffolds where the geometry (e.g., cyclic molecules, molecules with variable distances between domains, etc), orientation, stoichiometry, and valency can be systematically controlled outside that of what is enabled by classical polypeptide engineering. This restriction of production technologies places an enormous constraint on the therapeutic space that current formats can investigate. Current protein engineering methods are limited to the intrinsic repertoire of natural polypeptide folds/peptide linkers to achieve a desired construct. Therefore, non-natural formats that may exhibit greater efficacy cannot be prepared using conventional engineering methods. Further, due to toxicity constraints or the metabolic profiles of the expression hosts, some effector molecules cannot be effectively produced together in a one culture system. Additionally, correct folding, assembly, and purification of larger molecules becomes more difficult as the complexity of the molecule is increased, thereby decreasing yield and increasing cost.

Further, industrial production of antibody molecules generally requires expression of antibodies or antibody-like fragments in eukaryotic hosts, which are less robust than prokaryotic hosts and have reduced product yields compared to prokaryotic hosts, resulting in higher operating costs relative to antibodies or antibody-like fragments that can be expressed in prokaryotic hosts.

Thus, there exists a need in the art for a cost effective method of preparing next generation antibody therapeutics with high molecular weights that allows for the creation of a diverse library of antibody-like drugs with altered valency, geometry, effector function and stoichiometry simply by the combination of a comparatively small number of building blocks.

SUMMARY

One aspect of the disclosure provides constructs comprising a first fusion protein, a second fusion protein, and a linker, wherein the first fusion protein and the second fusion protein each include an affinity reagent and a reactive enzyme, and the linker includes a first functional group specific for irreversibly inhibiting the first fusion protein reactive enzyme at a first terminus, and a second functional group specific for irreversibly inhibiting the second fusion protein reactive enzyme at a second terminus.

Another aspect of the disclosure provides a method including (a) contacting a first fusion protein including an affinity reagent and a reactive enzyme with a linker including a functional group specific for irreversibly inhibiting the first fusion protein reactive enzyme at a first terminus thereby coupling the first fusion protein and the linker at the first terminus, and (b) contacting a second fusion protein including an affinity reagent and a reactive enzyme with a second terminus of the linker, the second terminus of the linker including a functional group specific for irreversibly inhibiting the second fusion protein reactive enzyme thereby coupling the second fusion protein and the linker at the second terminus.

Another aspect of the disclosure provides a construct prepared by the method of the disclosure.

Another aspect of the disclosure provides a method comprising administering a construct of the disclosure to a patient in need thereof. Other aspects of the disclosure provide uses of the construct of the disclosure as a medicament and/or as a diagnostic.

Further aspects and advantages will be apparent to those of ordinary skill in the art from a review of the following detailed description. While the constructs and their methods of making and use are susceptible of embodiments in various forms, the description hereafter includes specific embodiments with the understanding that the disclosure is illustrative, and is not intended to limit the invention to the specific embodiments described herein.

DETAILED DESCRIPTION

Figure 1:
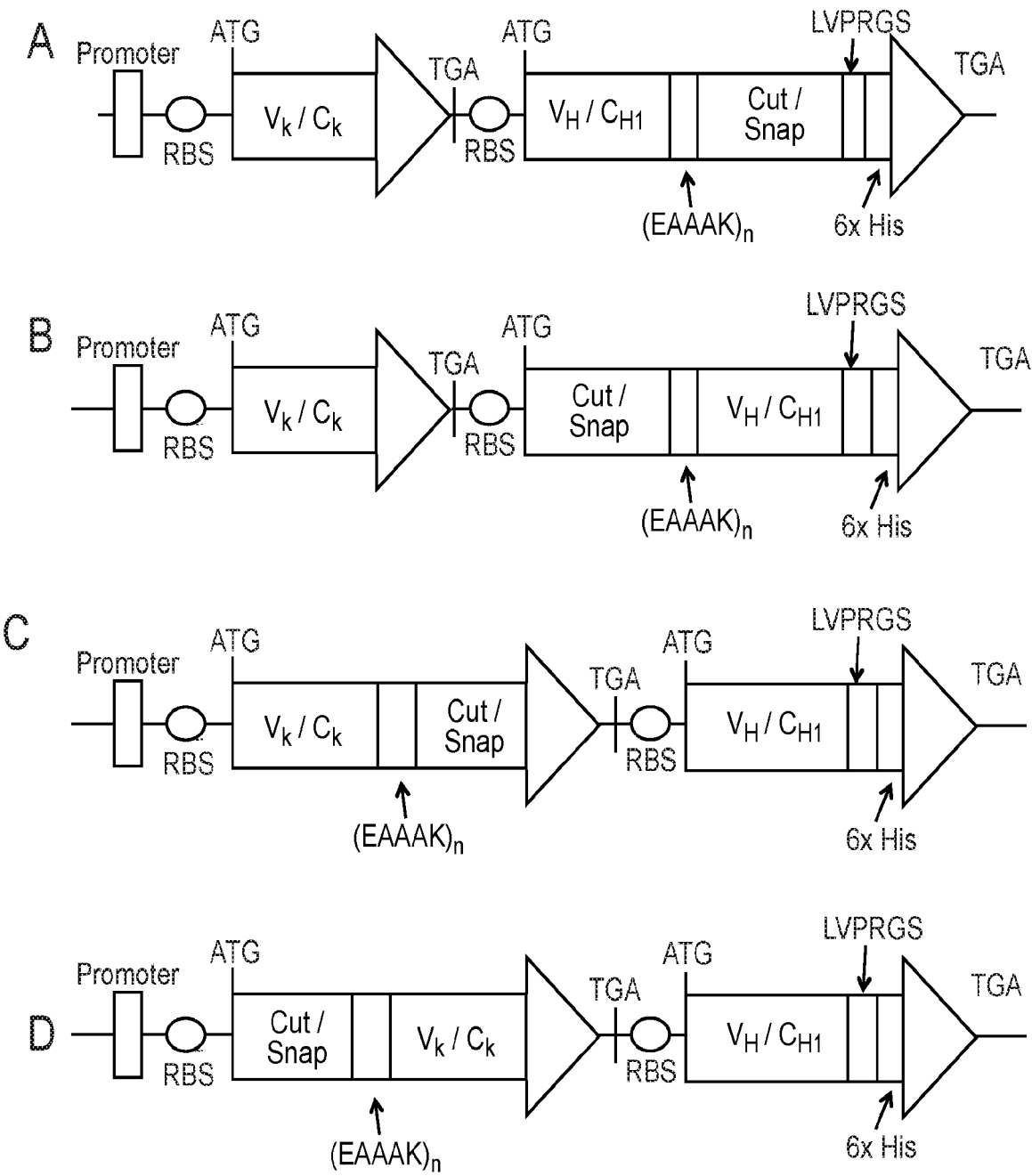
FIG. 1 shows Trastuzumab F(ab) (TFab) fusion gene/protein constructs.

Provided herein are constructs and methods of making and using the constructs. The constructs comprise a first fusion protein, a second fusion protein, and a linker, wherein the first fusion protein and the second fusion protein each include an affinity reagent and a reactive enzyme, and the linker includes a first functional group specific for irreversibly inhibiting the first fusion protein reactive enzyme at a first terminus, and a second functional group specific for irreversibly inhibiting the second fusion protein reactive enzyme at a second terminus. In embodiments, the first fusion protein reactive enzyme and the second fusion protein reactive enzyme are different. In embodiments, the first fusion protein reactive enzyme and the second fusion protein reactive enzyme are the same. In embodiments, the first fusion protein affinity reagent and the second fusion protein affinity reagent are different. In embodiments, the first fusion protein affinity reagent and the second fusion protein affinity reagent are the same. Optionally, in embodiments, each affinity reagent is independently selected from the group consisting of antibody or fragment thereof, small molecule, monobody, protein, and combinations thereof.

Constructs of Fusion Proteins of Affinity Reagent and Reactive Enzymes

The disclosed constructs comprise fusion proteins of an affinity reagent and a reactive enzyme linked via a linker.

As used herein and unless specified otherwise, "affinity reagent" refers to a moiety that exhibits affinity for a desired target, for example, the ability to bind to a target epitope in a therapeutic system and/or bind or recognize an analyte in a biosensor system. Examples of affinity reagents include, but are not limited to, antibodies or fragments thereof, small molecules, monobodies, and proteins.

As used herein and unless specified otherwise, "reactive enzyme" refers to an enzyme comprising an active-site residue that can couple to a functional group specific for irreversibly inhibiting the active-site residue.

As used herein and unless specified otherwise, "protein" refers to naturally occurring polypeptides, polypeptides comprising natural and/or unnatural amino acids, proteins in phage, therapeutic proteins, and antibody domains either synthetically or naturally derived.

As used herein a "polypeptide" refers to a polymer comprised of amino acid residues. Polypeptides are understood in the art and include without limitation an antibody, an enzyme, a structural polypeptide, and a hormone. Polypeptides of the present disclosure may be either naturally occurring or non-naturally occurring.

Naturally occurring polypeptides include without limitation biologically active polypeptides (including antibodies) that exist in nature or can be produced in a form that is found in nature by, for example, chemical synthesis or recombinant expression techniques. Naturally occurring polypeptides also include lipoproteins and post-translationally modified proteins, such as, for example and without limitation, glycosylated proteins.

Antibodies contemplated for use in the methods and compositions of the present disclosure include without limitation antibodies that recognize and associate with a target molecule either in vivo or in vitro.

Structural polypeptides contemplated by the disclosure include without limitation actin, tubulin, collagen, elastin, myosin, kinesin and dynein.

Non-naturally occurring polypeptides contemplated by the present disclosure include but are not limited to synthetic polypeptides, as well as fragments, analogs and variants of naturally occurring or non-naturally occurring polypeptides as defined herein. Non-naturally occurring polypeptides also include proteins or protein substances that have D-amino acids, modified, derivatized, or non-naturally occurring amino acids in the D- or L-configuration and/or peptidomimetic units as part of their structure. The term "protein" typically refers to large polypeptides. The term "peptide" typically refers to short polypeptides.

Non-naturally occurring polypeptides are prepared, for example, using an automated polypeptide synthesizer or, alternatively, using recombinant expression techniques using a modified polynucleotide which encodes the desired polypeptide.

As used herein a "fragment" of a polypeptide is meant to refer to any portion of a polypeptide or protein smaller than the full-length polypeptide or protein expression product.

As used herein an "analog" refers to any of two or more polypeptides substantially similar in structure and having the same biological activity, but can have varying degrees of activity, to either the entire molecule, or to a fragment thereof. Analogs differ in the composition of their amino acid sequences based on one or more mutations involving substitution, deletion, insertion and/or addition of one or more amino acids for other amino acids. Substitutions can be conservative or non-conservative based on the physicochemical or functional relatedness of the amino acid that is being replaced and the amino acid replacing it.

As used herein a "variant" refers to a polypeptide, protein or analog thereof that is modified to comprise additional chemical moieties not normally a part of the molecule. Such moieties may modulate, for example and without limitation, the molecule's solubility, absorption, and/or biological half-life. Moieties capable of mediating such effects are disclosed in Remington's Pharmaceutical Sciences (1980). Procedures for coupling such moieties to a molecule are well known in the art.

Antibodies and fragments or derivatives thereof, including but not limited to Fab' fragments, F(ab)2 fragments, Fv fragments, Fc fragments, one or more complementarity determining regions (CDR) fragments, individual heavy chains, individual light chain, dimeric heavy and light chains (as opposed to heterotetrameric heavy and light chains found in an intact antibody, single chain antibodies (scAb), humanized antibodies (as well as antibodies modified in the manner of humanized antibodies but with the resulting antibody more closely resembling an antibody in a non-human species), chelating recombinant antibodies (CRABs), bispecific antibodies and multispecific antibodies, and other antibody derivative or fragments known in the art are contemplated.

In embodiments of the foregoing aspect, at least one antibody or fragment thereof of the construct includes trastuzumab or fragment thereof, raxibacumab or fragment thereof, tocilizumab or fragment thereof, brentuximab or fragment thereof, ofatumumab or fragment thereof, belimumab or fragment thereof, ramucirumab or fragment thereof, vedolizumab or fragment thereof, obinutuzumab or fragment thereof, pembrolizumab or fragment thereof, ranibizumab or fragment thereof, pertuzumab or fragment thereof, denosumab or fragment thereof, catumaxomab or fragment thereof, golimumab or fragment thereof, siltuximab or fragment thereof, natalizumab or fragment thereof, panitumumab or fragment thereof, denosumab or fragment thereof, and combinations of the foregoing.

In embodiments, the linker is a polyoxazoline, polyacrylomorpholine, polyvinylpyrrolidone, polyphosphazene, polyethylene-co-maleic acid anhydride, polystyrene-co-maleic acid anhydride, poly(1-hydroxymethylethylene hydroxymethyl formal) ("PHF"), a polyhydroxyalkylacrylate, 2-methyacryloyloxy-2'-ethyltrimethylammonium phosphate ("MPC"), or a structure selected from:

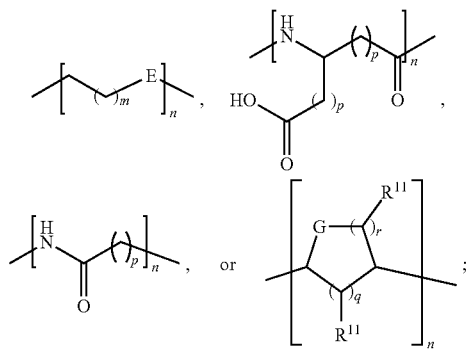

wherein: m is 0-10; n is 1-100; each p independently is 0, 1, 2, 3, or 4; q is 0, 1, or 2; r is 1 or 2; E is NH or $CHR^{10}$; G is O, $CH_2$, CHOH, $CHNH_2$, CHCOOH, or $CHSO_3H$; $R_{10}$ is OH, $NH_2$, or COOH; and each $R^{11}$ independently is H, OH, $NH_2$, or COOH.

In embodiments, each reactive enzyme is independently selected from the group consisting of cutinase, SnapTag, HaloTag, relaxase domains of type I DNA topoisomerases, beta-lactamase, glycosidase, matrix metalloproteinase, cytoplasmic protein tyrosine kinase domains, alkaline phosphatases, protein-tyrosine-phosphatases, mutants of 23S rRNA(adenine(2503)-C(2))-methyltransferases, glucosidases, N-6 adenine-specific DNA methylase, N(4)-cytosine-specific DNA methylase, DNA (cytosine-5-)-methyltransferase, mutants of haloalkane dehalogenases, HNH endonucleases, nicking endonucleases, gelatinases B, gelatinases A, stromelysins, fatty acid amide hydrolases, esterases, cytochrome P450s, methionine aminopeptidases, and combinations thereof. In embodiments, each reactive enzyme is independently selected from the group consisting of cutinase, the haloalkane dehydrogenase HaloTag, the mutant $O^6$-alkylguanine DNA alkyltransferase, SnapTag, relaxase domains of type I DNA topoisomerases, betalactamase, glycosidase, matrix metalloproteinase, and combinations thereof. In embodiments, each reactive enzyme is independently selected from the group consisting of cutinase, the haloalkane dehydrogenase HaloTag, the mutant $O^6$-alkylguanine DNA alkyltransferase, SnapTag, and combinations thereof.

In embodiments, the first fusion protein reactive enzyme and the second fusion protein reactive enzyme are different. In embodiments, the first fusion protein reactive enzyme and the second fusion protein reactive enzyme are the same. In embodiments, the first fusion protein affinity reagent and the second fusion protein affinity reagent are different. In embodiments, the first fusion protein affinity reagent and the second fusion protein affinity reagent are the same. Optionally, in embodiments, each affinity reagent is independently selected from the group consisting of antibody or fragment thereof, small molecule, monobody, protein, and combinations thereof.

In embodiments, the fusion proteins of the affinity reagent and the reactive enzyme are formed by conventional synthetic chemistry techniques to attach the reactive enzyme to the affinity reagent. In some cases, where the affinity reagent comprises a protein or antibody, a fusion protein is produced by expressing a polynucleotide sequence that encodes the affinity reagent and the reactive enzyme. In some aspects, the disclosure provides a vector comprising the polynucleotide operably linked to a promoter. In further aspects, the disclosure provides a host cell comprising the vector. In some embodiments, the host cell is an *Escherichia coli* cell. In further embodiments, the host cell is a mammalian cell. In related embodiments, the host cell is a Chinese Hamster Ovary (CHO) cell. In still further embodiments, the host cell is a yeast cell. In further aspects, a method of producing a fusion protein disclosed herein is provided, the method comprising the step of culturing a host cell of the disclosure under conditions appropriate to induce expression of the polypeptide. In related embodiments, the polypeptide is isolated.

Affinity Reagents

The constructs of the disclosure include fusion proteins which comprise an affinity reagent that provides functionality to the fusion protein. Thus, a construct comprising a first fusion protein and a second fusion protein having precisely defined structures and functions can be assembled. Examples of functionality imparted to the fusion protein through the affinity reagent include, but are not limited to, enhanced targeting of disease-related proteins in circulation or on cell surfaces, increased cytotoxicity, immunomodulation, drug delivery, use as contrast agents, use as diagnostic agents, or combinations of the foregoing.

The first affinity reagent and the second affinity reagent can be the same or different. Each affinity reagent can be independently selected from the group consisting of antibody or fragment thereof, small molecule, monobody, protein, and combinations thereof.

In embodiments, the affinity reagent comprises an antibody or fragment thereof. The antibody or fragment thereof can be selected from the group consisting of a light chain variable domain ($V_L$), a light chain constant domain ($C_L$), a heavy chain variable domain ($V_H$), a heavy chain constant domain ($C_H1$), and a combination thereof. The antibody or fragment thereof can be a chimeric antibody, a human antibody, and a humanized antibody. Examples of antibodies or fragments thereof include, but are not limited to, trastuzumab or fragment thereof, raxibacumab or fragment thereof, tocilizumab or fragment thereof, brentuximab or fragment thereof, ofatumumab or fragment thereof, belimumab or fragment thereof, ramucirumab or fragment thereof, vedolizumab or fragment thereof, obinutuzumab or fragment thereof, pembrolizumab or fragment thereof, ranibizumab or fragment thereof, pertuzumab or fragment thereof, denosumab or fragment thereof, catumaxomab or fragment thereof, golimumab or fragment thereof, siltuximab or fragment thereof, natalizumab or fragment thereof, panitumumab or fragment thereof, and denosumab or fragment thereof.

In embodiments, the affinity reagent comprises a small molecule. The small molecule can be a drug. Examples of small molecule drugs include, but are not limited to, aldesleukin, alendronic acid, alfaferone, alitretinoin, allopurinol, aloprim, aloxi, altretamine, aminoglutethimide, L-asparaginase, amifostine, amrubicin, amsacrine, anastrozole, anzmet, aranesp, arglabin, arsenic trioxide, aromasin, 5-azacytidine, azathioprine, BCG or tice-BCG, bestatin, betamethasone acetate, betamethasone sodium phosphate, bexarotene, bleomycin sulphate, broxuridine, bortezomib, bleomycin, busulfan, calcitonin, campath, capecitabine, carboplatin, carmustine, casodex, cefesone, celmoleukin, cerubidin, chlorambucil, cisplatin, colaspase, cladribin, clodronic acid, cyclophosphamide, cytarabine, dacarbazine, dactinomycin, daunoxome, decadron, decadron phosphate, delestrogen, denileukin diftitox, depomedrol, deslorelin, dexrazoxane, daunorubicin, diethylstilbestrol, 2',2'-difluorodeoxycytidine, diflucan, docetaxel, doxifluridine, doxorubicin, dronabinol, DW-166HC, eligard, elitek, ellence, emend, epirubicin, epoetin-alfa, epogen, eptaplatin, ergamisol, estrace, estradiol, estramustine sodium phosphate, ethinylestradiol, ethyol, etidronic acid, etopophos, etoposide, fadrozole, farstone, filgrastim, finasteride, fligrastim, floxuridine, fluconazole, fludarabin, fludarabin phosphate, 5-fluorodeoxyuridine, 5-fluorodeoxyuridine monophosphate, 5-fluorouracil (5-FU), fluoxymesterone, flutamide, hexamethylmelamine, formestane, fosteabine, fotemustine, fulvestrant, gammagard, gemcitabine, gemtuzumab, gleevec, gliadel, goserelin, granisetron hydrochloride, histrelin, hycamtin, hydrocortone, erythro-hydroxynonyladenine, hydroxyurea, hydroxyprogesterone caproate, ibritumomab tiuxetan, idarubicin, ifosfamide, interferon-alpha, interferon-alpha-2, interferon-alpha-2, interferon-alpha-2β, interferon-alpha-n1, interferon-alpha-n3, interferon-beta, interferon-gamma-la, interleukin-2, intron A, iressa, irinotecan, kytril, lentinan sulphate, letrozole, leucovorin, leuprolide, leuprolide acetate, levamisole, levofolic acid calcium salt, levothroid, levoxyl, lomustine, lonidamine, marinol, mechlorethamine, mecobalamin, medroxyprogesterone acetate, megestrol acetate, melphalan, menest, 6-mercaptopurine, mesna, methotrexate, metvix, miltefosine, minocycline, mitomycin C, mitotane, mitoxantrone, modrenal, myocet, nedaplatin, neulasta, neumega, neupogen, nilutamide, nolvadex, NSC-631570, OCT-43, octreotide, ondansetron hydrochloride, oraprep, oxaliplatin, paclitaxel, pediapred, pegaspargase, pegasys, pentostatin, N-phosphonoacetyl L-aspartate (PALA), picibanil, pilocarpine hydrochloride, pirarubicin, plicamycin, porfimer sodium, prednimustine, prednisolone, prednisone, premarin, procarbazine, procrit, raltitrexed, rebif, rhenium-186 etidronate, rituximab, roferon-A, romurtide, salagen, sandostatin, sargramostim, semustine, sizofiran, sobuzoxane, solu-medrol, streptozocin, strontium-89 chloride, Synthroid, tamoxifen, tamsulosin, tasonermin, tastolactone, taxoter, teceleukin, temozolomide, teniposide, testosterone propionate, testred, thioguanine, thiotepa, thyrotropin, tiludronic acid, topotecan, toremifen, tositumomab, tastuzumab, teosulfan, tretinoin, trexall, trimethylmelamine, trimetrexate, triptorelin acetate, triptorelin pamoate, UFT, uridine, valrubicin, vesnarinone, vinblastine, vincristine, vindesine, vinorelbine, virulizin, zinecard, zinostatin-stimalamer, zofran; ABI-007, acolbifen, actimmune, affinitak, aminopterin, arzoxifen, asoprisnil, atamestane, atrasentan, avastin, BAY 43-9006 (sorafenib), CCI-779, CDC-501, celebrex, cetuximab, crisnatol, cyproterone acetate, decitabine, DN-101, doxorubicin-MTC, dSLIM, dutasteride, edotecarin, eflornithine, exatecan, fenretinide, histamine dihydrochloride, histrelin hydrogel implant, holmium-166 DOTMP, ibandronic acid, interferon-gamma, intron-PEG, ixabepilone, keyhole limpet hemocyanine, L-651582, lanreotide, lasofoxifen, libra, lonafarnib, miproxifen, minodronate, MS-209, liposomal MTP-PE, MX-6, nafarelin, nemorubicin, neovastat, nolatrexed, oblimersen, onko-TCS, osidem, paclitaxel polyglutamate, pamidronate disodium, PN-401, QS-21, quazepam, R-1549, raloxifen, ranpirnas, 13-cis-retic acid, satraplatin, seocalcitol, T-138067, tarceva, taxoprexin, thymosin-alpha-1, tiazofurin, tipifarnib, tirapazamine, TLK-286, toremifen, trans-MID-107R, valspodar, vapreotide, vatalanib, verteporfin, vinflunin, Z-100, zoledronic acid and combinations of the foregoing.

In embodiments, the affinity reagent comprises a protein. In embodiments, the protein is selected from the group consisting of a natural protein, a natural amino acid, an unnatural amino acid, a protein in phage, a therapeutic protein, a synthetic antibody domain, and combinations of the foregoing. In embodiments, the protein is selected from the group consisting of an unnatural amino acid, a protein in phage, a therapeutic protein, a synthetic antibody domain, and combinations of the foregoing.

In embodiments, the affinity reagent is selected from the group consisting of designed ankyrin repeat proteins (DARPins), HEL4 Vh domains (Predator), Z-domain of staphylococcal protein A (Affibody), archaeal "7 kDa DNA binder" protein family (Affitin), carbohydrate-binding module (CBD domain), cystine-knot miniprotein (knottin), fibronectin type III domain (monobody, Adnectin), γ-B-crystallin (Affilin), cystatins (Affimers), triple helix coiled coil domains (Alhabodies), lipocalin domains (Anticalins), A domains of various membrane receptors (Avimers), SH3 domains of Fyn (Fynomers), Kunitz domain peptides, and combinations thereof.

Reactive Enzyme

The fusion proteins of the disclosure include a reactive enzyme that can couple to a functional group specific for irreversibly inhibiting the reactive enzyme that is present on a linker. Thus, a construct comprising a first fusion protein and a second fusion protein having precisely defined structures can be assembled using a modular approach using synthetic linkers that selectively couple to an active-site residue in the fusion protein reactive enzymes.

The first fusion protein reactive enzyme and the second fusion protein reactive enzyme can be the same or different. Each reactive enzyme can be independently selected from the group consisting of cutinase, SnapTag, HaloTag, relaxase domains of type I DNA topoisomerases, beta-lactamase, glycosidase, matrix metalloproteinase, cytoplasmic protein tyrosine kinase domains, alkaline phosphatases, protein-tyrosine-phosphatases, mutants of 23S rRNA(adenine (2503)-C(2))-methyltransferases, glucosidases, N-6 adenine-specific DNA methylase, N(4)-cytosine-specific DNA methylase, DNA (cytosine-5-)-methyltransferase, mutants of haloalkane dehalogenases, HNH endonucleases, nicking endonucleases, gelatinases B, gelatinases A, stromelysins, fatty acid amide hydrolases, esterases, cytochrome P450s, methionine aminopeptidases, and combinations thereof.

In embodiments, each reactive enzyme is independently selected from the group consisting of cutinase, HaloTag, SnapTag, relaxase domains of type I DNA topoisomerases, betalactamase, glycosidase, matrix metalloproteinase, and combinations thereof. In embodiments, each reactive enzyme is independently selected from the group consisting of cutinase, HaloTag, SnapTag, and combinations thereof.

In embodiments, the reactive enzyme is a mobility class (MOB) relaxase domain of type I DNA topoisomerases. The MOB relaxase domain of type-I DNA topoisomerases are enzymes that attach covalently to small cognate origin of transfer (oriT) DNA sequences located within a mobility plasmid that also encodes the relaxase protein. Such enzymes cleave the oriT DNA sequence at a specific nucleotide residue and covalently attach to the oriT DNA sequence at the point of cleavage. MOB relaxase domain of type I DNA topoisomerases can be characterized by family, wherein each family member has a similar structure and mechanism. Examples of known MOB relaxase domains of type-I DNA topoisomerase families include $MOB_F$, $MOB_H$, $MOB_Q$, $MOB_C$, $MOB_P$, and $MOB_V$. OriT sequences for members of each relaxase family are specific to the mobility plasmids from which each relaxase protein sequence is derived. Known examples of relaxase families and their associated plasmids include, but are not limited to, $MOB_F$ family: pF, pR100, pR388, pWWO, pMFLV02, pREB5, pREC1, and pNAC3; $MOB_H$ family: pR27, pCAR1, pSXT, pIP1202, pMOL28, and pPNAP01; $MOB_C$ family: pCloDF13, p23023, pCRY, pAD1, pSKU146.2, pLM7, and pSt0; $MOB_Q$ family: pRSF1010, pPRO2, pTi, pAt, pGOX3, pWCFS103, pBM300, pCAUL01, pTB3, pKJ50, and pRF; $MOB_P$ family: pRP4, pEST4011, pBI1063, pR64, pET46, pACRY04, pRAS3, pVirD2pTi, pColE1, pRA3, pVT745, pCP13, pFMC, pRP4, pR64, pK, pRAY, pCH4, pET35, pNP40, pCF10, pVir, pBOT3502, pMD136, pCIZ2, pS194, pSK639, and pRJ9; and $MOB_V$ family: pMV158, pE194, pUB110, pBBR1, pTn5520, pTn4555, pIncU, and pIncX, wherein the subscript "p" stands for plasmid.

Linkers

The linker includes at least a first terminus and a second terminus. The linker further includes at the first terminus, a first functional group specific for irreversibly inhibiting a fusion protein. The linker further includes at the second terminus, a second functional group specific for irreversibly inhibiting a fusion protein.

In embodiments, the linker further comprises a nitrogen-containing $C_{3-7}$heterocycle, polyoxazoline, polyacrylomorpholine, polyvinylpyrrolidone, polyphosphazene, polyethylene-co-maleic acid anhydride, polystyrene-co-maleic acid anhydride, poly(1-hydroxymethylethylene hydroxymethyl formal) ("PHF"), a polyhydroxyalkylacrylate (e.g., 2-hydroxyethylmethacrylate), 2-methyacryloyloxy-2'-ethyltrimethylammonium phosphate ("MPC"), or a combination thereof. For example, the linker can include polyoxazoline, polyacrylomorpholine, polyvinylpyrrolidone, polyphosphazene, polyethylene-co-maleic acid anhydride, polystyrene-co-maleic acid anhydride, PHF, a polyhydroxyalkylacrylate, or MPC.

In embodiments, the linker comprises a group selected from

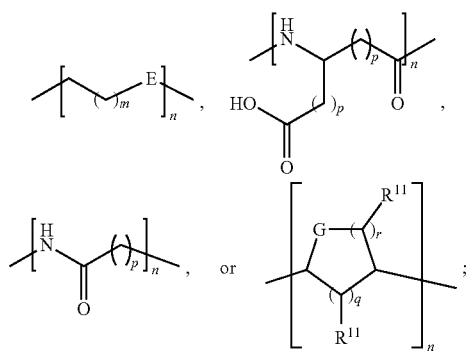

wherein:
m is 0-10;
n is 1-100;
each p independently is 0, 1, 2, 3, or 4;
q is 0, 1, or 2;
r is 1 or 2;
E is O, NH or $CHR^{10}$;
G is O, $CH_2$, CHOH, $CHNH_2$, CHCOOH, or $CHSO_3H$;
$R^{10}$ is OH, $NH_2$, or COOH; and
each $R^{11}$ independently is H, OH, $NH_2$, or COOH.

In embodiments, the linker comprises

In some embodiments, E is O. In various embodiments, E is NH. In some embodiments, E is $CHR^{10}$. For example E can include CHOH, $CHNH_2$, CHCOOH, or $CHSO_3H$. In these embodiments, m can be 0, 1, 2, 3, 4, 5, 6, 7, 8, 9, or 10. For example, m can be 1, 2, 3, 4, or 5. In some embodiments, m is 1, 2, or 3. In various embodiments, n can be 1-50, 1-40, 1-30, 1-20, 1-25, 1-20, 1-15, 1-10, or 1-5.

In embodiments, the linker comprises

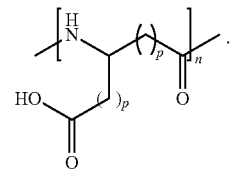

In some cases, p is 1, 2, or 3 (e.g., 1 or 2). For example, the linker can include aspartic acid, glutamic acid, or gamma-glutamic acid. In various embodiments, n can be 1-50, 1-40, 1-30, 1-20, 1-25, 1-20, 1-15, 1-10, or 1-5.

In embodiments, the linker comprises

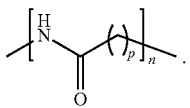

In some cases, p is 0, 1, 2, or 3 (e.g., 1 or 2). In various embodiments, n can be 1-50, 1-40, 1-30, 1-20, 1-25, 1-20, 1-15, 1-10, or 1-5.

In embodiments, the linker comprises

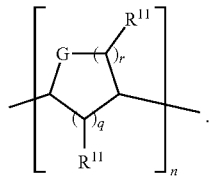

In embodiments, G is O. In embodiments wherein G is O, each $R^{11}$ can independently be H or OH. In embodiments, G is $CH_2$. In embodiments wherein G is $CH_2$, each $R^{11}$ can independently be H or OH, provided at least one $R^{11}$ is OH. In embodiments each $R^{11}$ is OH. In various embodiments wherein G is $CH_2$, each $R^{11}$ can independently be H or $NH_2$, provided at least one $R^{11}$ is $NH_2$. In various embodiments wherein G is $CH_2$, each $R^{11}$ can independently be H or COOH, provided at least one $R^{11}$ is COOH. In embodiments, G is CHOH. In embodiments wherein G is CHOH, each $R^{11}$ can independently be H or OH. In embodiments, each $R^{11}$ is OH. In embodiments, G is $CHNH_2$. In embodiments wherein G is $CHNH_2$, each $R^{11}$ can independently be H or $NH_2$. In embodiments, G is CHCOOH. In embodiments wherein G is CHCOOH, each $R^{11}$ can independently be H or COOH, provided at least one $R^{11}$ is COOH. In these embodiments, n can be 1-50, 1-40, 1-30, 1-20, 1-25, 1-20, 1-15, 1-10, or 1-5.

In embodiments, the linker includes a nitrogen-containing $C_{3-7}$heterocycle (e.g., pyrolidine, piperidine, piperazine), polyalkylene diamine (e.g., polyethylene diamine, polypropylene diamine, polybutylene diamine), a negatively charged amino acid (e.g., aspartic acid, glutamic acid, gamma-glutamic acid), or a saccharide (e.g., monosaccharide, polysaccharide, inositol, or polysialic acid).

In embodiments, the linker comprises polyalkylene oxide. The polyalkylene oxide can be linear or branched. For example the linker can include polyethylene glycol (e.g., PEG 40, PEG 100, PEG 150, PEG 200, PEG 300, PEG 2000), polypropylene glycol, or polybutylene glycol. The polyalkylene oxide can have a molecular weight of about 30 to about 5000 (e.g. about 30-4500, about 30-4000, about 30-3500, about 30-3000, about 30-2500, about 30-2000, about 30-1500, about 30-1000, about 46-1000, about 46-750, about 46-500, about 46-250, or about 46-100). Polyethylene oxide spacers, with and without reactive functionality at one or both of their termini, are well-known in the art and commercially available through, e.g., Quanta Biodesign, PierceNet, and SigmaAldrich.

Through the functional groups at the first and second termini, the linkers react with the fusion protein reactive enzymes site-specifically, in high yield, with rapid kinetics under mild conditions to provide at least a bivalent antibody construct. The functional groups at the linker termini can be any functional groups that irreversibly inhibit the reactive enzymes.

Examples of functional groups include, but are not limited to, p-nitrophenyl phosphonate, $O^6$-benzylguanine, α-haloalkane or derivative thereof, haloaromatic compound or derivative thereof, beta-lactam or derivative thereof such as clavulanic acid or derivative thereof, aglycone or derivative thereof, hydroxamic acid-benzophenones or derivative thereof, cognate oriT oligonucleotide sequence, cysteine-reactive ATP-binding site inhibitors, quinone methides or derivative thereof, α-halo phosphonic acids or precursor or derivative thereof, formylchromones or derivative thereof, cognate RNA sequence, adenosine or derivative thereof, cytosine or derivative thereof, cognate DNA nicking sites, thiiranes or derivative thereof, hydroxamic acids or derivative thereof, α-ketoxazole inhibitor or derivative thereof, electrophilic steroid, phosphonates, carbamates, aromatic alkynes, beloranib or derivative thereof, and combinations of the foregoing.

In embodiments, the functional group is selected from the group consisting of p-nitrophenyl phosphonate, $O^6$-benzylguanine, α-haloalkane or derivative thereof, haloaromatic compound or derivative thereof, beta-lactam or derivative thereof such as clavulanic acid or derivative thereof, aglycone or derivative thereof, hydroxamic acid-benzophenones or derivative thereof, cognate oriT oligonucleotide sequence, and combinations thereof. In embodiments, the functional group is selected from the group consisting of p-nitrophenyl phosphonate, $O^6$-benzylguanine, α-haloalkane or derivative thereof, haloaromatic compound or derivative thereof, and combinations thereof.

In embodiments, the functional group is a cognate oriT oligonucleotide sequence. In refinements of the foregoing embodiment, the cognate oriT oligonucleotide sequence is selected from the group consisting of 5'-TTTGCGTAGTGTGTGGTGCTTT-3' (SEQ ID NO: 1); 5'-TTTGCGTGGGGTGTGGTGCTTT-3'(SEQ ID NO: 2); 5'-TTTGCGTAGGGTGTGGTGCTTT-3' (SEQ ID NO: 3); 5'-CGCGCACCGAAAGGTGCGTATTGTCTATAGCCC-AGATTTAAGGA-3'(SEQ ID NO: 4); 5'-CCAT-TTCTCGAAGAGAAACCGGTAAATGCGCCCT-3'(SEQ ID NO: 5); 5'-CACACACTTTATGAATATAAAGTATA-GTGTTATACTTTA-3'(SEQ ID NO: 6); 5'ACGTTTCT-GAACGAAGTGAAGAAACGTCTAAGTGCGCCCT-3' (SEQ ID NO: 7) and combinations thereof.

In embodiments, the fusion protein reactive enzyme is a relaxase domain of type I DNA topoisomerases and the functional group is a cognate oriT oligonucleotide sequence. In embodiments, the relaxase domain of type I DNA topoisomerases (identified by mobility plasmids for each relaxase protein sequence)/cognate oriT oligonucleotide sequence pair is selected from the group consisting of pR100/5'-TTTGCGTAGTGTGTGGTGCTTT-3' (SEQ ID NO: 1); pF/5'-TTTGCGTGGGGTGTGGTGCTTT-3'(SEQ ID NO: 2); TraI$_{P307}$/5'-TTTGCGTAGGGTGTGGTGCTTT-3'(SEQ ID NO: 3); pR388/5'-CGCGCACCGAAAGGTGCGTAT-TGTCTATAGCCCAGATTTAAGGA-3'(SEQ ID NO: 4); pR1162/5'-CCATTTCTCGAAGAGAAACCGGT-AAATGCGCCCT-3' (SEQ ID NO: 5); pMobMN199/5'-CACACACTTTATGAATATAAAGTATAGTGT-TATACTTTA-3' (SEQ ID NO: 6); pSC101/5'ACGTTTCT-GAACGAAGTGAAGAAACGTCTAAGTGCGCCCT-3' (SEQ ID NO: 7), and combinations thereof.

In embodiments, the first fusion protein reactive enzyme comprises cutinase and the functional group at the first terminus comprises a p-nitrophenyl phosphonate.

In embodiments, the first fusion protein reactive enzyme comprises SnapTag and the functional group at the first terminus comprises an $O^6$-benzylguanine.

In embodiments, the first fusion protein reactive enzyme comprises HaloTag and the functional group at the first terminus comprises an α-chloroalkane.

In embodiments, the first fusion protein reactive enzyme comprises beta-lactamase and the functional group at the first terminus comprises a beta-lactam or derivative thereof.

In embodiments, the first fusion protein reactive enzyme comprises glycosidase and the functional group at the first terminus comprises an aglycone or a derivative thereof.

In embodiments, the first fusion protein reactive enzyme comprises matrix metalloproteinase and the functional group at the first terminus comprises hydroxamic acid-benzophenones or derivative thereof.

In embodiments, the first fusion protein reactive enzyme comprises a relaxase domain of type I DNA topoisomerases and the functional group at the first terminus comprises a cognate oriT oligonucleotide sequence.

In embodiments, the first fusion protein reactive enzyme comprises a cytoplasmic protein tyrosine kinase domain and the functional group at the first terminus comprises a cysteine-reactive ATP-binding site inhibitor.

In embodiments, the first fusion protein reactive enzyme comprises an alkaline phosphatase and the functional group at the first terminus comprises a functional group selected from the group consisting of quinone methides, α-halo phosphonic acid, precursor of the foregoing, derivative of the foregoing, and combinations of the foregoing.

In embodiments, the first fusion protein reactive enzyme comprises a protein-tyrosine-phosphatase and the functional group at the first terminus comprises a functional group selected from the group consisting of a formylchromone, α-halo phosphonic acid, precursor of the foregoing, derivative of the foregoing, and combinations of the foregoing.

In embodiments, the first fusion protein reactive enzyme comprises a mutant of 23S rRNA (adenine(2503)-C(2))-methyltransferase and the functional group at the first terminus comprises cognate RNA sequence.

In embodiments, the first fusion protein reactive enzyme comprises glucosidase and the functional group at the first terminus comprises aglycone or derivative thereof.

In embodiments, the first fusion protein reactive enzyme comprises N-6 adenine-specific DNA methylase and the functional group at the first terminus comprises adenosine or derivative thereof.

In embodiments, the first fusion protein reactive enzyme comprises N(4)-cytosine-specific DNA methylase and the functional group at the first terminus comprises cytosine or derivative thereof.

In embodiments, the first fusion protein reactive enzyme comprises DNA (cytosine-5-)-methyltransferase and the functional group at the first terminus comprises cytosine or derivative thereof.

In embodiments, the first fusion protein reactive enzyme comprises mutants of haloalkane dehalogenases and the functional group at the first terminus comprises a functional group selected from the group consisting of haloalkanes, haloaromatic compounds, or derivative thereof.

In embodiments, the first fusion protein reactive enzyme comprises HNH endonucleases and the functional group at the first terminus comprises cognate DNA nicking sites.

In embodiments, the first fusion protein reactive enzyme comprises nicking endonucleases and the functional group at the first terminus comprises cognate DNA nicking sites.

In embodiments, the first fusion protein reactive enzyme comprises gelatinase B and the functional group at the first terminus comprises a functional group selected from the group consisting of thiiranes, hydroxamic acids, derivatives of the foregoing, and combinations of the foregoing.

In embodiments, the first fusion protein reactive enzyme comprises gelatinase A and the functional group at the first terminus comprises a functional group selected from the group consisting of thiiranes, hydroxamic acids, derivatives of the foregoing, and combinations of the foregoing.

In embodiments, the first fusion protein reactive enzyme comprises stromelysins and the functional group at the first terminus comprises a functional group selected from the group consisting of thiiranes, hydroxamic acids, derivatives of the foregoing, and combinations of the foregoing.

In embodiments, the first fusion protein reactive enzyme comprises a fatty acid amide hydrolase and the functional group at the first terminus comprises an α-ketoxazole inhibitor or derivative thereof.

In embodiments, the first fusion protein reactive enzyme comprises esterases and the functional group at the first terminus comprises a functional group selected from the group consisting of phosphonates, carbamates, derivatives of the foregoing, and combinations of the foregoing.

In embodiments, the first fusion protein reactive enzyme comprises cytochrome P450s and the functional group at the first terminus comprises a functional group selected from the group consisting of electrophilic steroids, aromatic alkynes, derivatives of the foregoing, and combinations of the foregoing.

In embodiments, the first fusion protein reactive enzyme comprises methionine aminopeptidases and the functional group at the first terminus comprises beloranib or derivative thereof.

In embodiments, the second fusion protein reactive enzyme comprises cutinase and the functional group at the second terminus comprises a p-nitrophenyl phosphonate.

In embodiments, the second fusion protein reactive enzyme comprises SnapTag and the functional group at the second terminus comprises an $O^6$-benzylguanine.

In embodiments, the second fusion protein reactive enzyme comprises HaloTag and the functional group at the second terminus comprises an α-chloroalkane.

In embodiments, the second fusion protein reactive enzyme comprises beta-lactamase and the functional group at the second terminus comprises a beta-lactam or a derivative thereof.

In embodiments, the second fusion protein reactive enzyme comprises glycosidase and the functional group at the second terminus comprises an aglycone or a derivative thereof.

In embodiments, the second fusion protein reactive enzyme comprises matrix metalloproteinase and the functional group at the second terminus comprises hydroxamic acid-benzophenone or a derivative thereof.

In embodiments, wherein the second fusion protein reactive enzyme comprises a relaxase domain of type I DNA topoisomerases and the functional group at the second terminus comprises a cognate oriT oligonucleotide sequence.

In embodiments, the second fusion protein reactive enzyme comprises a cytoplasmic protein tyrosine kinase domain and the functional group at the second terminus comprises a cysteine-reactive ATP-binding site inhibitor.

In embodiments, the second fusion protein reactive enzyme comprises an alkaline phosphatase and the functional group at the second terminus comprises a functional group selected from the group consisting of quinone methides, α-halo phosphonic acid, precursor of the foregoing, derivative of the foregoing, and combinations of the foregoing.

In embodiments, the second fusion protein reactive enzyme comprises a protein-tyrosine-phosphatase and the functional group at the second terminus comprises a functional group selected from the group consisting of a formylchromone, α-halo phosphonic acid, precursor of the foregoing, derivative of the foregoing, and combinations of the foregoing.

In embodiments, the second fusion protein reactive enzyme comprises a mutant of 23S rRNA (adenine(2503)-C(2))-methyltransferase and the functional group at the second terminus comprises cognate RNA sequence.

In embodiments, the second fusion protein reactive enzyme comprises glucosidase and the functional group at the second terminus comprises aglycone or derivative thereof.

In embodiments, the second fusion protein reactive enzyme comprises N-6 adenine-specific DNA methylase and the functional group at the second terminus comprises adenosine or derivative thereof.

In embodiments, the second fusion protein reactive enzyme comprises N(4)-cytosine-specific DNA methylase and the functional group at the second terminus comprises cytosine or derivative thereof.

In embodiments, the second fusion protein reactive enzyme comprises DNA (cytosine-5-)-methyltransferase and the functional group at the second terminus comprises cytosine or derivative thereof.

In embodiments, the second fusion protein reactive enzyme comprises mutants of haloalkane dehalogenases and the functional group at the second terminus comprises a functional group selected from the group consisting of haloalkanes, haloaromatic compounds, or derivative thereof.

In embodiments, the second fusion protein reactive enzyme comprises HNH endonucleases and the functional group at the second terminus comprises cognate DNA nicking sites.

In embodiments, the second fusion protein reactive enzyme comprises nicking endonucleases and the functional group at the second terminus comprises cognate DNA nicking sites.

In embodiments, the second fusion protein reactive enzyme comprises gelatinase B and the functional group at the second terminus comprises a functional group selected from the group consisting of thiiranes, hydroxamic acids, derivatives of the foregoing, and combinations of the foregoing.

In embodiments, the second fusion protein reactive enzyme comprises gelatinase A and the functional group at the second terminus comprises a functional group selected from the group consisting of thiiranes, hydroxamic acids, derivatives of the foregoing, and combinations of the foregoing.

In embodiments, the second fusion protein reactive enzyme comprises stromelysins and the functional group at the second terminus comprises a functional group selected from the group consisting of thiiranes, hydroxamic acids, derivatives of the foregoing, and combinations of the foregoing.

In embodiments, the second fusion protein reactive enzyme comprises a fatty acid amide hydrolase and the functional group at the second terminus comprises an α-ketoxazole inhibitor or derivative thereof.

In embodiments, the second fusion protein reactive enzyme comprises esterases and the functional group at the second terminus comprises a functional group selected from the group consisting of phosphonates, carbamates, derivatives of the foregoing, and combinations of the foregoing.

In embodiments, the second fusion protein reactive enzyme comprises cytochrome P450s and the functional group at the second terminus comprises a functional group selected from the group consisting of electrophilic steroids, aromatic alkynes, derivatives of the foregoing, and combinations of the foregoing.

In embodiments, the second fusion protein reactive enzyme comprises methionine aminopeptidases and the functional group at the second terminus comprises beloranib or derivative thereof.

Methods of Preparing Constructs

Another aspect of the disclosure provides a method including (a) contacting a first fusion protein including an affinity reagent and a reactive enzyme with a linker including a functional group specific for irreversibly inhibiting the first fusion protein reactive enzyme at a first terminus thereby coupling the first fusion protein and the linker at the first terminus, and (b) contacting a second fusion protein including an affinity reagent and a reactive enzyme with a second terminus of the linker, the second terminus of the linker including a functional group specific for irreversibly inhibiting the second fusion protein reactive enzyme thereby coupling the second fusion protein and the linker at the second terminus.

As used herein and unless specified otherwise, "coupled," "couple," or "coupling" encompasses covalent bond formation, for example, through which the fusion protein can irreversibly associate with the functional group at the linker terminus.

The method disclosed here joins fusion proteins including affinity reagents and reactive enzymes in a modular fashion using small molecule linkers that have functional groups at the termini which react site specifically with the reactive enzymes in high yield with rapid kinetics under mild reaction conditions.

The methods disclosed herein provide one or more advantages, for example, providing a means by which an incredibly diverse population of therapeutic constructs can be generated in a modular fashion. Additionally, the preparation of antibody formats with expanded functionality is straightforward using the constructs of the disclosure, as no reactive amino acids need to be engineered/functionalized directly on an antibody scaffold. Further, the mild, rapid, and site-specific nature of the coupling of the fusion proteins and the linkers allows for diverse effector molecules to be attached to an antibody fragment in precise stoichiometry in high yield and away from the antibody-like fragment. Further still, molecules that cannot be expressed in homologous hosts with antibody fragments such as toxins or glycosylated proteins can be expressed in various organisms and attached in a modular fashion to the construct. Modular synthesis permits the creation of molecules too large or complex to prepare using standard protein engineering/expression as such methods require polypeptides to be expressed as one or more chains in culture.

The chemical linking modular approach enables an efficient method to produce precisely-defined protein constructs of variable stoichiometry, orientation, and geometry. These attributes can be systematically altered by encoding diversity into the linkers and/or by altering the order of attachment of the fusion proteins to the linkers. Current protein engineering methods are limited to the intrinsic repertoire of natural polypeptide folds/peptide linkers to achieve a desired construct. Therefore, non-natural formats that may exhibit greater efficacy cannot be prepared using conventional engineering methods.

Finally, the expression of smaller antibody-like fragments enables expression in prokaryotic hosts in addition to the eukaryotic hosts typically used in the industrial production of antibody molecules. It is well known that the robustness of prokaryotes, in addition to product yields that are often 5× those of eukaryotic expression systems, enables a lower cost manufacturing platform.

Another aspect of the disclosure provides a construct prepared by the method of the disclosure.

In embodiments, step (a) and (b) are performed sequentially (i.e., stepwise). In embodiments, step (a) and (b) are performed contemporaneously (i.e., one pot). Each affinity reagent and reactive enzyme can be selected from any of the affinity reagents and reactive enzymes disclosed herein. The linker, including the functional group at the first terminus and the functional group at the second terminus, can be selected from any of the linkers and functional groups disclosed herein.

In embodiments, the first fusion protein reactive enzyme and the second fusion protein reactive enzyme are the same and the functional group specific for irreversibly inhibiting the first fusion protein reactive enzyme at the first terminus of the linker is the same as the functional group specific for irreversibly inhibiting the second fusion protein reactive enzyme at the second terminus of the linker, and steps (a) and (b) are performed contemporaneously.

In embodiments, the first fusion protein reactive enzyme and the second fusion protein reactive enzyme are the same and the functional group specific for irreversibly inhibiting the first fusion protein reactive enzyme at the first terminus of the linker is different from the functional group specific for irreversibly inhibiting the second fusion protein reactive enzyme at the second terminus of the linker, and steps (a) and (b) are performed contemporaneously.

In embodiments, the first fusion protein reactive enzyme and the second fusion protein reactive enzyme are different and the functional group specific for irreversibly inhibiting the first fusion protein reactive enzyme at the first terminus of the linker is the same as the functional group specific for irreversibly inhibiting the second fusion protein reactive enzyme at the second terminus of the linker, and steps (a) and (b) are performed sequentially.

In embodiments, the first fusion protein reactive enzyme and the second fusion protein reactive enzyme are different and the functional group specific for irreversibly inhibiting the first fusion protein reactive enzyme at the first terminus of the linker is the same as the functional group specific for irreversibly inhibiting the second fusion protein reactive enzyme at the second terminus of the linker, and steps (a) and (b) are performed contemporaneously.

In embodiments, the first fusion protein reactive enzyme and the second fusion protein reactive enzyme are different and the functional group specific for irreversibly inhibiting the first fusion protein reactive enzyme at the first terminus of the linker is different from the functional group specific for irreversibly inhibiting the second fusion protein reactive enzyme at the second terminus of the linker, and steps (a) and (b) are performed contemporaneously.

In embodiments, the first fusion protein reactive enzyme and the second fusion protein reactive enzyme are different and the functional group specific for irreversibly inhibiting the first fusion protein reactive enzyme at the first terminus of the linker is different from the functional group specific for irreversibly inhibiting the second fusion protein reactive enzyme at the second terminus of the linker, and steps (a) and (b) are performed sequentially.

The method disclosed herein provides one or more advantages such as allowing the scalable preparation of molecules with molecular weights greater than about 100 kDa, about 150 kDa, about 200 kDa, about 250 kDa and/or about 300 kDa and/or creation of diverse libraries of antibody-like drugs with altered valency, geometry, effector function, and stoichiometry simply by the combination of a comparatively smaller number of building blocks.

Steps (a) and (b) can be performed in any aqueous solution buffered to a physiological pH, for example, phosphate-buffered saline (PBS) at pH 7.4. The concentration of the first fusion protein, second fusion protein, and linker can generally be any concentration. The concentration is typically chosen such that the first fusion protein, second fusion protein, and linker are fully soluble in a chosen solvent, without forming saturated solutions. When the linker comprises only a functional group specific for irreversibly inhibiting an enzyme at a first terminus and a second terminus, the relative concentration of first fusion protein to linker to second fusion protein is at least about 1:1:1 to provide one functional group specific for irreversibly inhibiting an enzyme linker terminus per fusion protein.

In embodiments, steps (a) and (b) are performed at ambient temperatures. The temperature should not be so high as to denature any proteins present in the fusion proteins.

In embodiments, the constructs can be prepared on a solid support. In embodiments, one or more components of step (a) and/or (b) can be provided on a solid support. Suitable solid supports are well known in the art.

Methods of Using the Constructs

Another aspect of the disclosure provides a method comprising administering a construct of the disclosure to a patient in need thereof. Yet another aspect of the disclosure provide uses of the construct of the disclosure as a medicament for a patient in need thereof. Another aspect of the disclosure provides the use of the construct of the disclosure as a diagnostic.

In embodiments, the patient suffers from a disorder or disease selected from the group consisting of breast cancer, inhalational anthrax, rheumatoid arthritis, systemic juvenile idiopathic arthritis, Hodgkin lymphoma, chronic lymphocytic leukemia, follicular non-Hodgkin's lymphoma, diffuse large B cell lymphoma, relapsing remitting multiple sclerosis, systemic lupus erythematosus, gastric or gastro-esophageal junction adenocarcinoma, metastatic non-small-cell lung carcinoma, ulcerative colitis, Crohn's disease, melanoma, macular degeneration, osteoporosis, treatment-induced bone loss, metastases to bone, giant cell tumor of bone, malignant ascites, psoriatic arthritis, ankylosing spondylitis, metastatic renal cell cancer, prostate cancer, ovarian cancer, multiple myeloma, Castleman's disease, colorectal cancer, and combinations of the foregoing.

As used herein and unless specified otherwise, "disease" and "disorder" are used interchangeably.

In embodiments, at least one antibody or fragment thereof of the construct includes trastuzumab or fragment thereof, raxibacumab or fragment thereof, tocilizumab or fragment thereof, brentuximab or fragment thereof, ofatumumab or fragment thereof, belimumab or fragment thereof, ramucirumab or fragment thereof, vedolizumab or fragment thereof, obinutuzumab or fragment thereof, pembrolizumab or fragment thereof, ranibizumab or fragment thereof, pertuzumab or fragment thereof, denosumab or fragment thereof, catumaxomab or fragment thereof, golimumab or fragment thereof, siltuximab or fragment thereof, natalizumab or fragment thereof, panitumumab or fragment thereof, denosumab or fragment thereof, and combinations of the foregoing.

In embodiments, the patient suffers from breast cancer and at least one antibody or fragment thereof of the construct comprises trastuzumab or a fragment thereof.

In embodiments, the patient suffers from inhalational anthrax and at least one antibody or fragment thereof of the construct comprises raxibacumab or fragment thereof.

In embodiments, the patient suffers from rheumatoid arthritis or systemic juvenile idiopathic arthritis and at least one antibody or fragment thereof of the construct comprises tocilizumab or fragment thereof.

In embodiments, the patient suffers from Hodgkin lymphoma or systemic anaplastic large cell lymphoma and at least one antibody or fragment thereof of the construct comprises brentuximab or fragment thereof.

In embodiments, the patient suffers from a condition selected from the group consisting of chronic lymphocytic leukemia, follicular non-Hodgkin's lymphoma, diffuse large B cell lymphoma, rheumatoid arthritis, and relapsing remitting multiple sclerosis, and at least one antibody or fragment thereof of the construct comprises ofatumumab or fragment thereof.

In embodiments, the patient suffers from systemic lupus erythematosus and at least one antibody or fragment thereof of the construct comprises belimumab or fragment thereof.

In embodiments, the patient suffers from gastric or gastroesophageal junction adenocarcinoma or metastatic non-small-cell lung carcinoma and at least one antibody or fragment thereof of the construct comprises ramucirumab or fragment thereof.

In embodiments, the patient suffers from ulcerative colitis or Crohn's disease and at least one antibody or fragment thereof of the construct comprises vedolizumab or fragment thereof.

In embodiments, the patient suffers from chronic lymphocytic leukemia or follicular lymphoma and at least one antibody or fragment thereof of the construct comprises obinutuzumab or fragment thereof.

In embodiments, the patient suffers from melanoma or metastatic non-small cell lung cancer and at least one antibody or fragment thereof of the construct comprises pembrolizumab or fragment thereof.

In embodiments, the patient suffers from macular degeneration and at least one antibody or fragment thereof of the construct comprises ranibizumab or fragment thereof.

In embodiments, the patient suffers from breast cancer and at least one antibody or fragment thereof of the construct comprises pertuzumab or fragment thereof.

In embodiments, the patient suffers from a condition selected from the group consisting of osteoporosis, treatment-induced bone loss, metastases to bone, and giant cell tumor of bone and at least one antibody or fragment thereof of the construct comprises denosumab or fragment thereof.

In embodiments, the patient suffers from malignant ascites and at least one antibody or fragment thereof of the construct comprises catumaxomab or fragment thereof.

In embodiments, the patient suffers from a condition selected from the group consisting of rheumatoid arthritis, psoriatic arthritis, ankylosing spondylitis, and ulcerative colitis and at least one antibody or fragment thereof of the construct comprises golimumab or fragment thereof.

In embodiments, the patient suffers from a condition selected from the group consisting of metastatic renal cell cancer, prostate cancer, ovarian cancer, non-Hodgkin's lymphoma, multiple myeloma, and Castleman's disease and at least one antibody or fragment thereof of the construct comprises siltuximab or fragment thereof.

In embodiments, the patient suffers from multiple sclerosis or Crohn's disease and at least one antibody or fragment thereof of the construct comprises natalizumab or fragment thereof.

In embodiments, the patient suffers from colorectal cancer and at least one antibody or fragment thereof of the construct comprises panitumumab or fragment thereof.

In embodiments, the patient suffers from a condition selected from the group consisting of osteoporosis, treatment-induced bone loss, metastases to bone, and giant cell tumor of bone and at least one antibody or fragment thereof of the construct comprises denosumab or fragment thereof.

The constructs, methods, and uses in accordance with the disclosure can be better understood in light of the following examples, which are merely intended to illustrate the constructs and are not meant to limit the scope thereof in any way.

EXAMPLES

Example 1: Gene/Protein Expression Vector Construction of F(Ab) Domains from Trastuzumab Genes encoding the F(ab) domains (light chain variable $V_L$—light chain constant kappa chain $C_K$, and heavy chain variable domain $V_H$—heavy chain constant domain $C_H1$) from monoclonal antibody trastuzumab (hereafter designated "TFab(s)") were synthesized with codon optimization for *E. coli* by Genscript. The following eight dicistronic fusion proteins were assembled in a tetracycline-inducible expression vector based on pASK-IBA32 (IBA Biosciences) using restriction free PCR:

1. "N-terminal cutinase-$V_L$ fusion"-5'-RBS1-ATG-cutinase-(EAAAK)$_2$-$V_L C_K$--RBS2-ATG-$V_H C_H$1-LVPRGS-HHHHHH--3' (SEQ ID NOs: 8 & 9)
2. "N-terminal SnapTag-$V_L$ fusion"-5'-RBS1-ATG-SnapTag-(EAAAK)$_2$-$V_L C_K$--RBS2-ATG-$V_H C_H$1-LVPRGS-HHHHHH--3' (SEQ ID NOs: 10 & 11)
3. "C-terminal cutinase-$C_K$ fusion"-5'-RBS1-ATG-$V_L C_K$-(EAAAK)$_2$-cutinase--RBS2-ATG-$V_H C_H$1-LVPRGS-HHHHHH--3' (SEQ ID NOs: 12 & 13)
4. "C-terminal SnapTag-$C_K$ fusion"-5'-RBS1-ATG-$V_L C_K$-(EAAAK)$_2$-SnapTag--RBS2-ATG-$V_H C_H$1-LVPRGS-HHHHHH--3' (SEQ ID NO: 14 & 15)
5. "N-terminal cutinase-$V_H$ fusion"-5'-RBS1-ATG-$V_L C_K$--RBS2-ATG-cutinase-(EAAAK)$_2$-$V_H C_H$1-LVPRGS-HHHHHH--3' (SEQ ID NO: 16 & 17)
6. "N-terminal SnapTag-$V_H$ fusion"-5'-RBS1-ATG-$V_L C_K$--RBS2-ATG-SnapTag-(EAAAK)$_2$-$V_H C_H$1-LVPRGS-HHHHHH--3' (SEQ ID NO: 18 & 19)
7. "C-terminal cutinase-$C_H$1 fusion"-5'-RBS1-ATG-$V_L C_K$--RBS2-ATG-$V_H C_H$1-(EAAAK)$_2$-cutinase-LVPRGS-HHHHHH--3' (SEQ ID NO: 20 & 21)
8. "C-terminal SnapTag-CHI fusion"-5'-RBS1-ATG-$V_L C_K$--RBS2-ATG-$V_H C_H$1-(EAAAK)$_2$-SnapTag-LVPRGS-HHHHHH--3' (SEQ ID NO: 22 & 23)

FIG. 1 shows the Trastuzumab F(ab) (TFab) fusion gene/protein constructs. A) C-terminal heavy chain fusions. B) N-terminal heavy chain fusions. C) C-terminal light chain fusions. D) N-terminal light chain fusions.

Example 2: Protein Expression/Purification

Vectors encoding the eight TFab fusion proteins of Example 1 were transformed into Shuffle *E. coli* (New England Biolabs). Expression cultures containing growth media (500 mL 2×YT), carbenicillin (200 μg/mL) and spectinomycin (50 μg/mL) were inoculated with an overnight culture (5 mL) of cell stocks bearing the appropriate expression cassette. Cultures were grown at 30° C. with shaking at 250 rpm until reaching an optical dispersion (OD) of about 0.8. At this point, anhydrotetracycline (aTc) was added to the cultures at final concentration of 200 ng/mL to induce protein expression. Cultures were maintained at 24° C. with shaking at 250 rpm for 14 hr during the expression phase.

After expression, cells were harvested via centrifugation and lysed via chemical disruption using 35 ml. CelLytic B (Sigma Aldrich) containing DNAse I, and EDTA-free protease inhibitors (Roche). Cell lysates were cleared of debris by centrifugation and added to a column containing cobalt IMAC resin (3 mL bed volume). Lysates were incubated for an hour over the beads with agitation at 4° C. After this period, beads were washed extensively with phosphate buffered saline (PBS) and the products then eluted with imidazole containing buffer (20 mL). Protein eluates were then purified first on a protein L column (GE Healthcare) followed by size exclusion chromatography (SEC) on a Superdex 200 column (GE Healthcare) via a fast protein liquid chromatography (FPLC) instrument. All column purifications via FPLC were done according to manufacturer's suggested protocols. Fractions containing pure protein products were pooled and concentrated in centrifugal concentrators prior to linking reactions.

Figure 2:
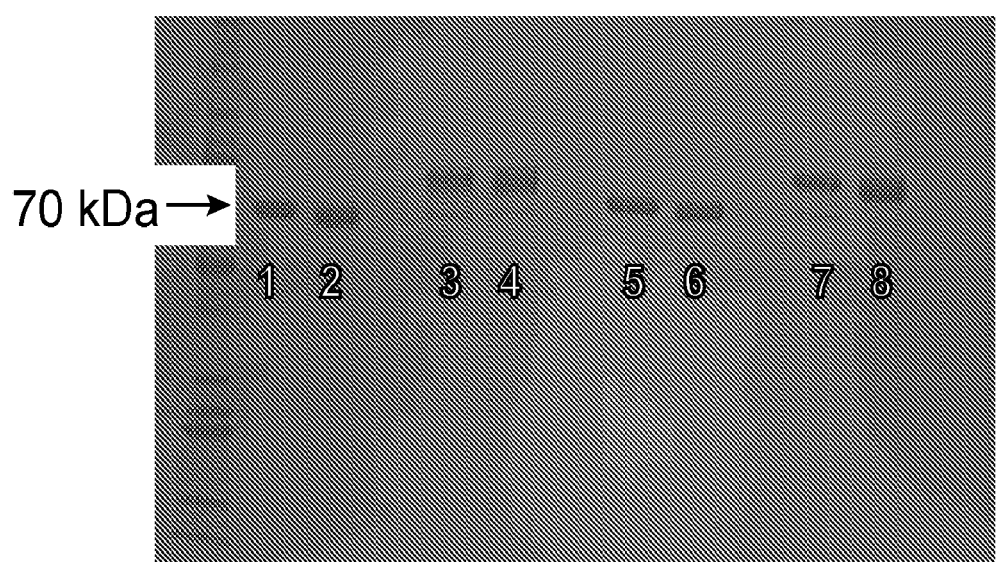
FIG. 2 shows the SDS-PAGE gel of purified TFab-cutinase and TFab-SnapTag fusions.
Figure 3:
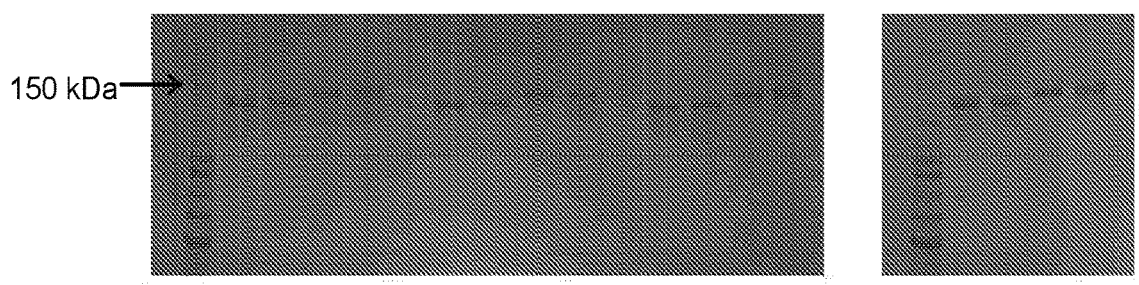
FIG. 3 shows the SDS-PAGE gel of bivalent constructs.

FIG. 2 shows the sodium dodecylsulfate polyacrylamide (SDS-PAGE) gel of purified TFab-cutinase and TFab-SnapTag fusions. Lanes 1 & 2 show bands near the calculated molecular weights for the N-terminal $V_H$ fusions of cutinase (72 kDa) and SnapTag (69 kDa) respectively. Lanes 3 & 4 show bands from C-terminal $V_H$ fusions. Lanes 5 & 6 and 7 & 8, show bands from C-terminal $C_K$ and $C_{H1}$ fusions, respectively.

Thus, Examples 1 and 2 show the preparation of fusion proteins of the disclosure comprising an affinity reagent (TFab) and a reactive enzyme (cutinase and/or SnapTag).

Example 3: Preparation of a Linker for Joining a Cutinase-TFab Fusion Protein with a SnapTag-TFab Fusion Protein

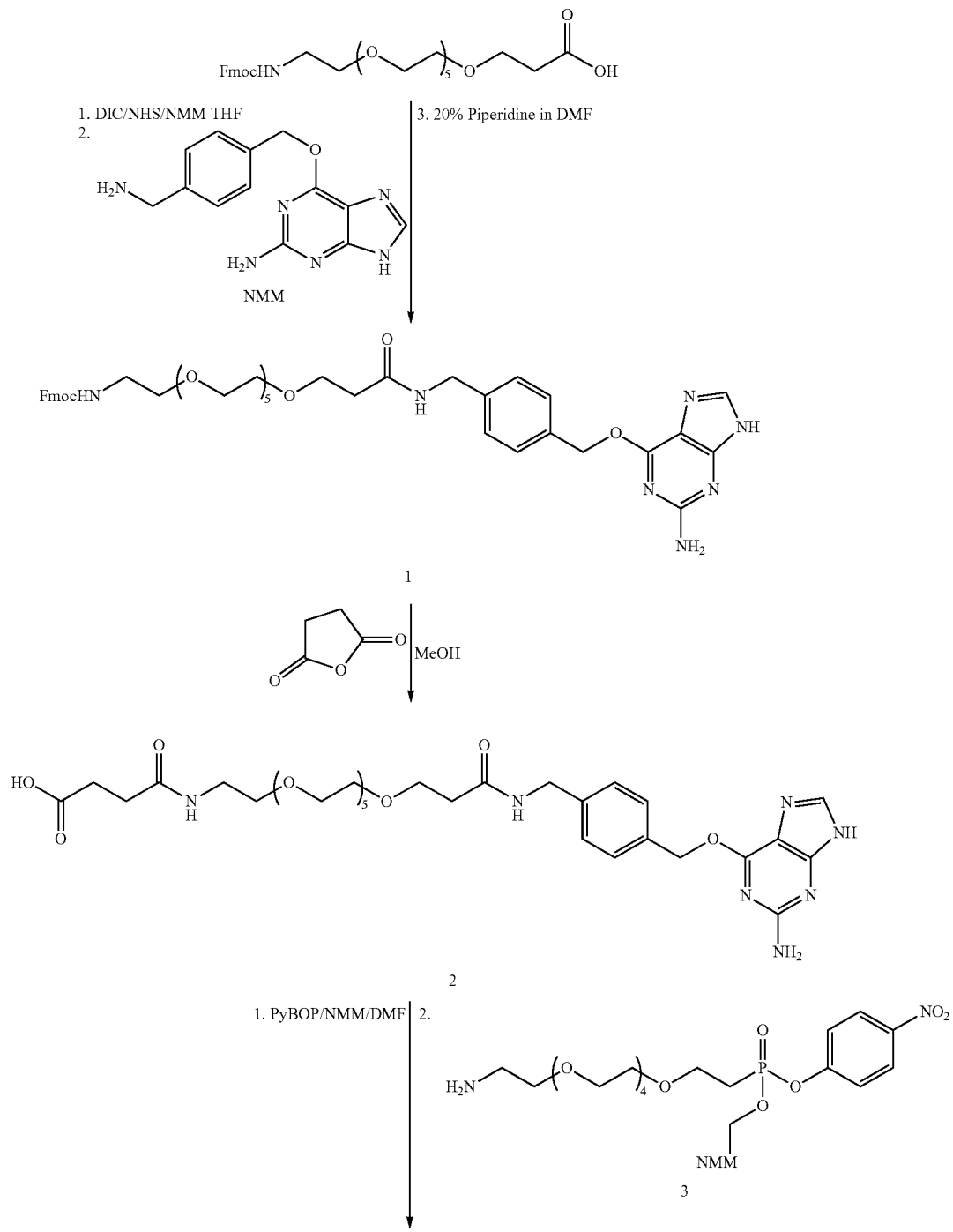

-continued

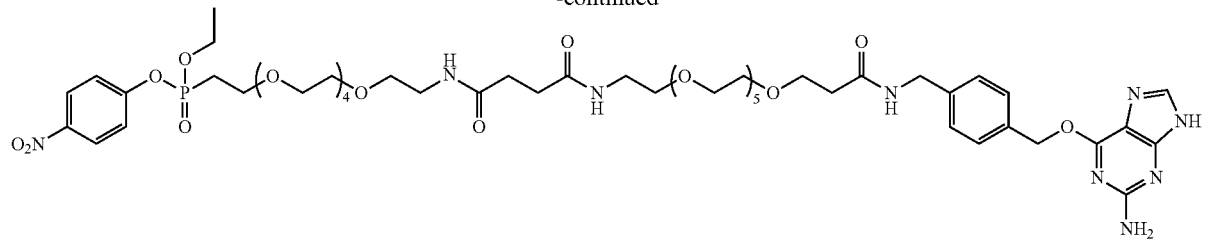

A linker according to the disclosure comprising a p-nitrophenyl phosphonate at the first terminus, an $O^6$-benzylguanine at the second terminus, and ethylene glycol and amide units was prepared according to the synthetic scheme shown below.

Preparation of 1-amino-N-(4-(((2-amino-9H-purin-6-yl)oxy)methyl)benzyl)-3,6,9,12,15,18-hexaoxahenicosan-21-amide (1). Fmoc-21-amino-4,7,10,13,16,19-hexaoxaheneicosanoic acid (567 mg, 0.99 mmol) was dissolved in 5 mL THF. To this solution was added DIC (149 mg, 183 µL, 1.18 mmol) followed by NHS (136 mg, 1.18 mmol) and the reaction was allowed to stir overnight at room temperature. The solvent was removed on a rotary evaporator and the resulting yellow oil was resuspended in 5 mL DMF. To this solution was added (4-aminomethyl)-$O^6$-benzylguanine (266 mg, 0.99 mmol) and the reaction allowed to stir 2 days at room temperature. After this period, the DMF was stripped from the reaction under a stream of $N_2$ overnight. The resulting orange oil was then treated with 5 mL 20% piperidine in MeOH and allowed to stir 1 hr at room temperature. The solvent was removed using a rotary evaporator and the resulting orange oil resuspended in 10 mL $H_2O$. This solution was then centrifuged to pellet insoluble material and the clarified supernatant applied in 5 separate portions to a reversed phase Cis column via a Waters Delta 400 HPLC. Elution was carried out using a linear gradient of 75% ACN in deionized ultra-filtered water (DIUF)+ 0.01% TFA over 60 min with DIUF+0.01% TFA as the mobile phase at a flow rate of 10 mL/min. Fractions from 20-35 min were then analyzed by MALDI-MS. Pure fractions were pooled and lyophilized to yield an amber oil. (424 mg, 71%)

Preparation of 1-(4-4-(((2-amino-9H-purin-6-yl)oxy)methyl)phenyl)-3,25-dioxo-6,9,12,15,18,21-hexaoxa-2,24-diazaoctacosan-28-oic acid (2). Compound 1 (50 mg, 83 µmol) was dissolved in 2.5 mL MeOH and to this solution was added succinic anhydride (8.3 mg, 83 µmol). Upon completion of the reaction (~30 min as monitored by MALDI-MS), the solvent was removed on a rotary evaporator. The resulting amber oil was then purified via silica gel chromatography first using 10:1 $CH_2Cl_2$:MeOH to remove impurities and then by elution with MeOH to yield a gummy amber solid. (42 mg, 72%)

The preparation of intermediate (3), 17-(ethoxy(4-nitrophenoxy)phosphoryl)-3,6,9,12,15-pentaoxaheptadecan-1-aminium chloride, is described in Modica, J. A. et al., Chembiochem. 2012 Nov. 5; 13(16):2331-4, which is hereby incorporated by reference in its entirety.

Preparation of ethyl (4-nitrophenyl) (1-(4-(((2-amino-9H-purin-6-yl)oxy)methyl)phenyl)-3,25,28-trioxo-6,9,12,15,18,21,32,35,38,41,44-undecaoxa-2,24,29-triazahexatetracontan-46-yl)phosphonate (4). Compound 2 (39 mg, 55 µmol) was dissolved in 1 mL DMF. To this solution was added PyBOP (34 mg, 58 µmol) followed by N-methylmorpholine (5.6 mg, 6.1 µL, 55 µmol) and the reaction was allowed to stir for 30 min at room temperature. After this period, compound 3 (29.3 mg, 55 µmol) dissolved in 250 µL DMF was added to the mixture followed by N-methylmorpholine (11.2 mg, 12.2 µL, 110 µmol) and the reaction was allowed to stir overnight (~16 hr). After this period, the mixture was diluted to 5 mL using DIUF and the mixture centrifuged to remove insoluble material. The clarified supernatant was then and injected onto a $C_{18}$ semi-prep scale column via a Waters Delta 4000 HPLC and purified using a linear gradient of 75% aqueous ACN+0.1% TFA over 70 min with DIUF+0.1% TFA as the mobile phase at a flow rate of 10 mL/min. Fractions were collected at a rate of 1/min. Fractions from 25-40 min were then analyzed by MALDI. Those containing pure product were pooled, frozen at −80° C. and lyophilized to yield a yellow oil. This oil was then subjected to one additional round of HPLC purification using the aforementioned procedure. Pure fractions from this run were pooled, frozen and lyophilized to yield a light yellow oil (11 mg, 17%).

Thus, Example 3 shows the preparation of a linker of the disclosure comprising a first functional group specific for irreversibly inhibiting a first fusion protein reactive enzyme at a first terminus, and a second functional group specific for irreversibly inhibiting a second fusion protein reactive enzyme at a second terminus.

Example 4: Di-TFab Construct Assembly

Equal volumes of cutinase-TFab fusion (5 µM) and SnapTag-TFab fusion (5 µM) from Example 2 and cutinase-SnapTag linker (5 µM) from Example 3 in PBS pH 7.4 were mixed and allowed to react for 4 hr. After the reaction, products were purified via size-exclusion chromatography.

Figure 5:
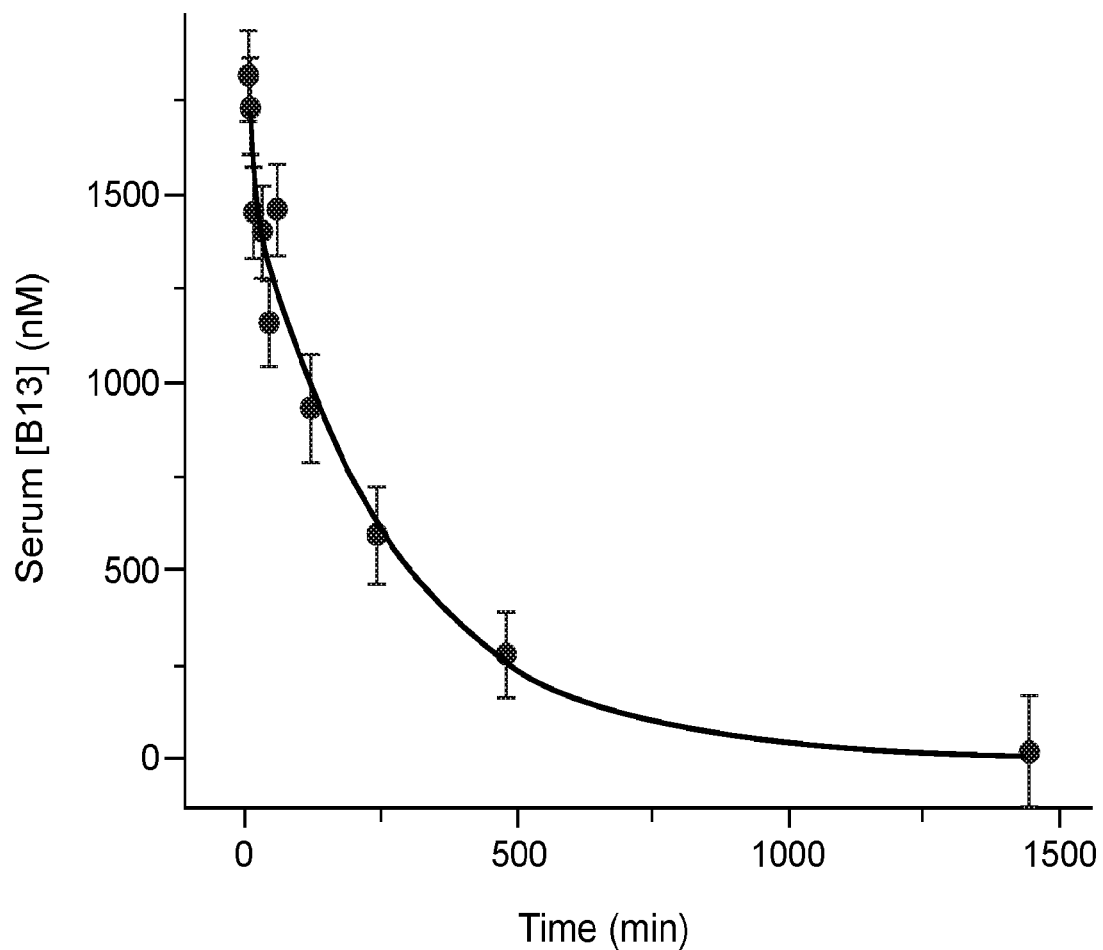
FIG. 5 is a plot of serum concentration of the B-13 construct in mice over time.

FIG. 5 shows SDS-PAGE gels of the constructs prepared. From a pool of 8 TFabs and one linker, 16 bivalent analog constructs can be produced.

Thus, Example 4 shows preparation of a library of constructs of the disclosure comprising a first fusion protein, a second fusion protein, and a linker, wherein the first fusion protein and the second fusion protein each comprises an affinity reagent and a reactive enzyme; and the linker comprises a first functional group specific for irreversibly inhibiting the first fusion protein reactive enzyme at a first terminus, and a second functional group specific for irreversibly inhibiting the second fusion protein reactive enzyme at a second terminus.

Example 5: Cell Growth Inhibition Assay

Trastuzumab is employed in the treatment of HER2+ breast cancers. Two HER2 (+++) cell lines (BT474, SKBR3), one HER2 (++) cell line (MDA-MB-VII-135) and one control cell line AT-431 (HER2−) were cultured according to established protocols and treated with doses of Trastuzumab or one of the bivalent trastuzumab analogs prepared in Example 4 in concentrations ranging from 4 µM to 4 µM for 96 h. Viability after this period was determined using the Alamar blue assay (Life Technologies). Viabilities were calculated as percentage values vs. untreated controls.

Figure 4:
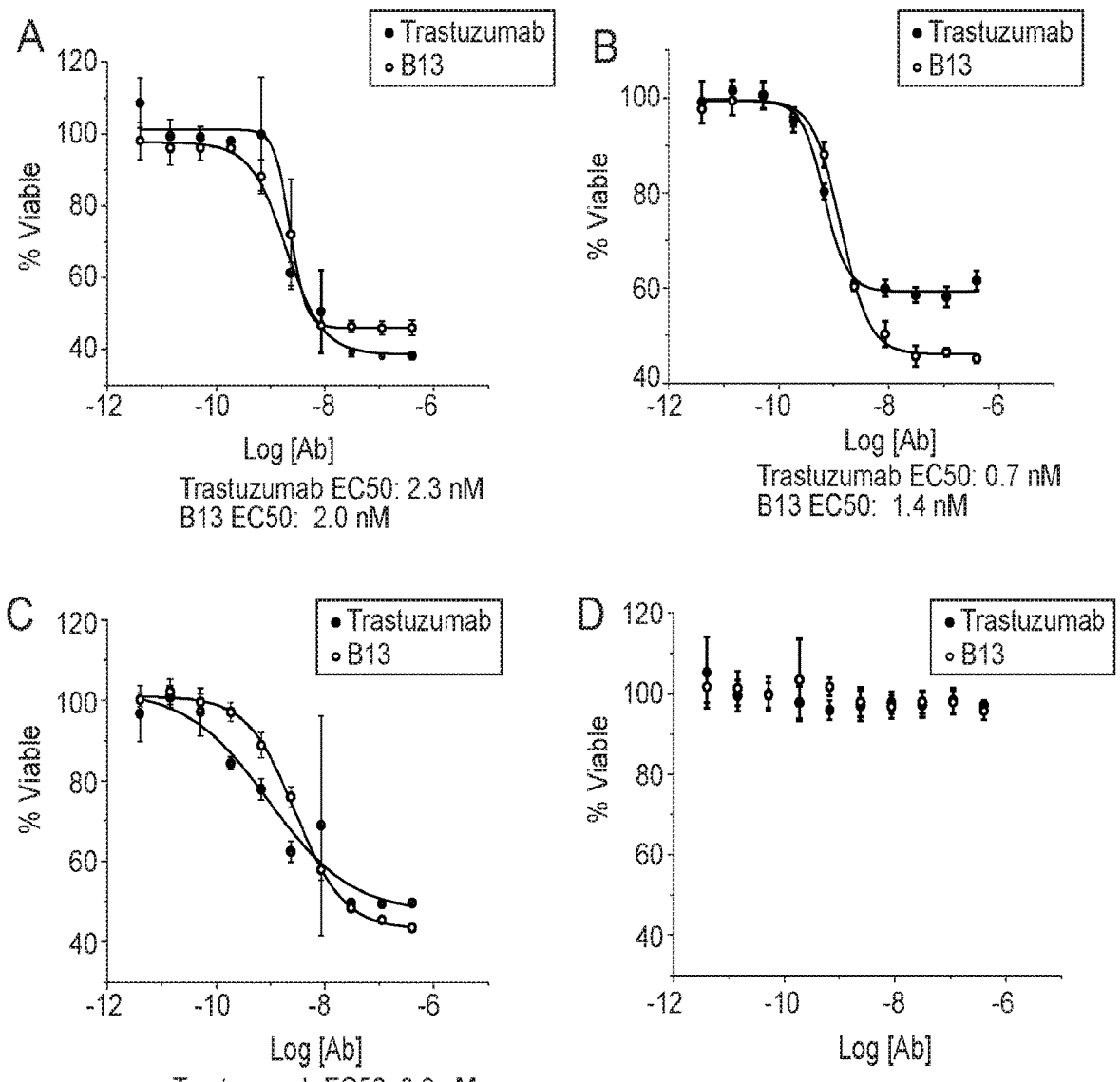
FIG. 4 shows cell viability assay data of trastuzumab and a fusion protein construct, B-13.

From these experiments, one construct, designated B-13, showed the most favorable cell growth inhibition and EC50 value vs. Trastuzumab. Cell viability experiments were performed again with B-13 vs. Trastuzumab. FIG. 4 shows the cell viability assay data showing comparable cell growth inhibition by trastuzumab and B-13 in various cell lines. A) Growth inhibition of BT474 cells. B) Growth inhibition of SKBR3 cells. C) Growth inhibition of MDA-MB-135-VII cells. D) Control experiment using HER2(−) AT-431 cells showing no growth inhibition for trastuzumab or B-13.

Thus, Example 5 shows how libraries of constructs of the disclosure can be assayed for biological uses, for example, cell growth inhibition. Further, Example 5 shows cytotoxicity of the constructs in in vitro cancer cell viability assays. The fusion protein construct assembly method of Example 3 enables the preparation of multifunctional antibody-like therapeutic molecules in a one pot fashion.

Example 6: In Vivo Pharmacokinetics of Di-TFab Constructs

The B-13 construct (2 mg/mL) was administered as an IV bolus to SCID-beige mice at a total dose of 10 mg/kg. Blood samples (~200 µL) were drawn from tail veins at various time points post administration. A total of three mice (n=3) were treated and sampled for each time point. An ELISA method was used to determine the concentration of B13 in the serum via standard curve comparison. As shown in FIG. 5, these data were plotted and fitted to a two compartment (biexponential) pharmacokinetic model to yield an elimination rate constant of 0.22 hr$^{-1}$ and a half-life of 3.1 hr.

Thus, Example 6 shows in vivo use of the fusion protein constructs of the disclosure and the pharmacokinetic data of a construct of the disclosure.

Example 7—Effect of B-13 Administration on Mice Bearing BT474 Tumor Xenografts

Figure 6:
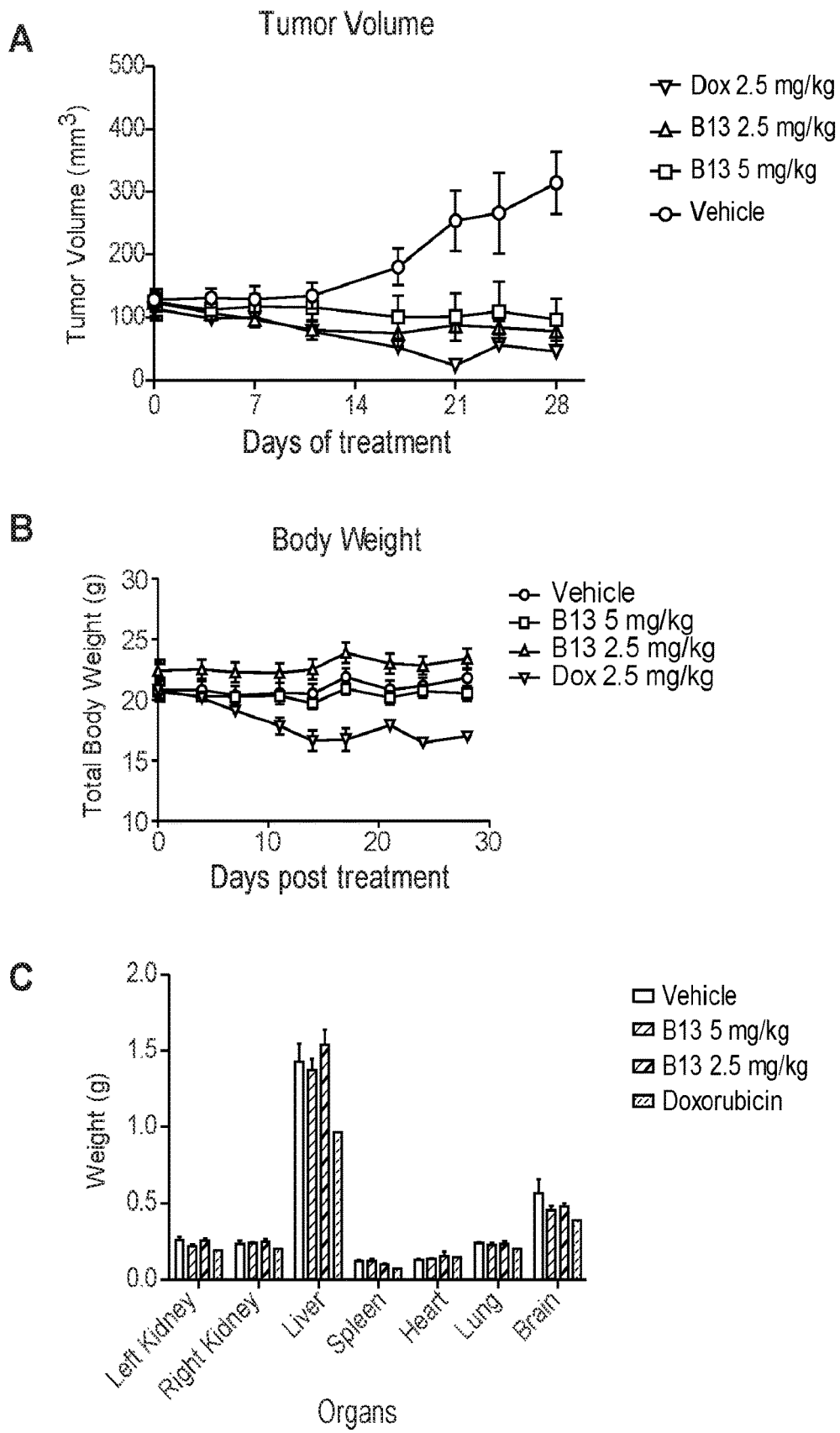
FIG. 6 shows the results of the effect of B-13 administration on mice having BT474 tumor xenogragfts. A) Tumor volume progression of the animals treated over 4 weeks with vehicle, B13 at 2.5 and 5 mg/kg daily, and doxorubicin (dox) twice a week at 2.5 mg/kg. At day 28, there is a significant difference in tumor volume between vehicle vs. doxorubicin ($p=0.0002$) and vehicle vs. the two B13 treatment groups ($p=0.0001$). B) Total body weight measurement of the animals in the four treatment cohorts. There is a significant difference in total body weight between vehicle and doxorubicin (p=0.0116) but no significant difference between vehicle and B13 treatment at 2.5 mg/kg (p=0.2237) or 5 mg/kg (p=0.4297) C) Organ weight of the animals in the four treatment cohorts. There is no significant difference in organ weight among the groups (p=0.9493). P-values were calculated using a Two Way ANOVA, in Graph Pad 7.0.

Eight-week-old female SCID beige mice were obtained from Charles River Laboratories and implanted with 0.025-mg, 90-day release, 17β-estradiol pellets (Innovative Research of America). After 2 days, 2×10$^6$ BT474 cells were resuspended in 100 µl of PBS and 1:1 mixture with Matrigel was inoculated orthotopically into the mammary gland fat pad. Once tumors reached a volume of ~150 mm$^3$, 20 animals were randomly assigned into four treatment cohorts (n=5) with equal average tumor volumes. In one cohort, B13 was administered by intraperitoneal (IP) injection five times per week (Monday-Friday) over 4 weeks in a total of twenty doses of 5 mg kg$^{-1}$; in a second cohort, B13 was administered via the same route and frequency at a dose of 2.5 mg/kg. In a third cohort, doxorubicin (dox), was administered via IP injection twice weekly in a total of eight doses over 4 weeks at 2.5 mg/kg. A control cohort was injected five times per week with vehicle (PBS+0.004% (w/w) Polysorbate 20). B13 and dox solutions were both formulated in the same vehicle. B13 samples contained <1.0 endotoxin units (EU)/mL as determined by limulus amebocyte lysate (LAL) assay. Tumor dimensions were serially measured every 2 days, and volumes calculated using the formula $V=(L \times W^2)/2$, where V=volume, L=length and W=width. The results are shown in FIG. 6.

B13 shows significant anti-tumor activity in a BT474 mouse xenograft model. Furthermore, B13, at the two doses used in this study, shows no outward signs of toxicity. This is in contrast to dox where the treatment cohort showed significant weight loss.

The foregoing description is given for clearness of understanding only, and no unnecessary limitations should be understood therefrom, as modifications within the scope of the invention may be apparent to those having ordinary skill in the art.

What is claimed:

1. A construct comprising
a first fusion protein, a second fusion protein, and a linker, wherein
  the first fusion protein and the second fusion protein each comprises an affinity reagent and a reactive enzyme; and
  the linker comprises a first functional group specific for irreversibly inhibiting the first fusion protein reactive enzyme at a first terminus, and a second functional group specific for irreversibly inhibiting the second fusion protein reactive enzyme at a second terminus, wherein the first functional group specific for irreversibly inhibiting the first fusion protein reactive enzyme is coupled to the first fusion protein reactive enzyme and the second functional group specific for irreversibly inhibiting the second fusion protein reactive enzyme is coupled to the second fusion protein reactive enzyme, such that the first fusion protein and second fusion protein are linked in the form of the construct, and
  wherein the first fusion protein reactive enzyme comprises cutinase and the second fusion protein reactive enzyme comprises HaloTag or SnapTag; and
  wherein the first fusion protein affinity reagent and the second fusion protein affinity reagent each comprise an antibody or fragment thereof,
  wherein the antibody fragment comprises Fab' fragments, F(ab)2 fragments, Fv fragments, Fc fragments, one or more complementarity determining regions (CDR) fragments, an individual heavy chain, an individual light chain, or a dimeric heavy and light chain.

2. The construct of claim 1, wherein the antibody or fragment thereof is selected from the group consisting of a light chain variable domain ($V_L$), a light chain constant domain ($C_L$), a heavy chain variable domain ($V_H$), a heavy chain constant domain ($C_H1$), and a combination thereof.

3. The construct of claim 1, wherein the antibody or fragment thereof is selected from the group consisting of adalimumab, alemtuzumab, arcitumomab, cetuximab, trastuzumab, imciromab, capromab, infliximab, abciximab, rituximab, basiliximab, palivizumab, nofetumomab, omalizumab, daclizumab, ibritumomab tiuxetan, muromonab, edrecolomab gemtuzumab ozogamicin, golimumab, certolizumab, eculizumab, ustekinumab, panitumumab, tositumomab, bevacizumab, raxibacumab, tocilizumab, brentuximab, ofatumumab, belimumab, ramucirumab, vedolizumab, obinutuzumab, pembrolizumab, ranibizumab, pertuzumab, denosumab, catumaxomab, golimumab, siltuximab, natalizumab, panitumumab, and denosumab.

4. The construct of claim 1, wherein the antibody or fragment thereof is a synthetic antibody domain.

5. The construct of claim 1, wherein the linker is a polyoxazoline, polyacrylomorpholine, polyvinylpyrrolidone, polyphosphazene, polyethylene-co-maleic acid anhydride, polystyrene-co-maleic acid anhydride, poly(1-hydroxymethylethylene hydroxymethyl formal) ("PHF"), a polyhydroxyalkylacrylate, 2-methyacryloyloxy-2'-ethyltrimethylammonium phosphate ("MPC"), or a structure selected from:

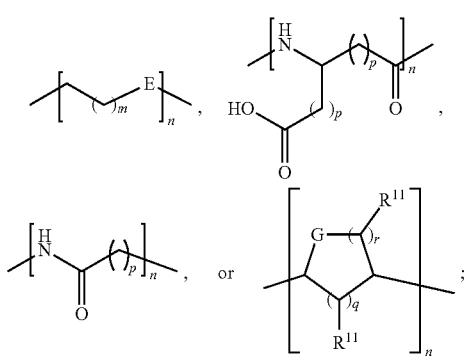

wherein:
m is 0-10;
n is 1-100;
each p independently is 0, 1, 2, 3, or 4;
q is 0, 1, or 2;
r is 1 or 2;
E is NH or $CHR^{10}$;
G is O, $CH_2$, CHOH, $CHNH_2$, CHCOOH, or $CHSO_3H$;
$R^{10}$ is OH, $NH_2$, or COOH;
each $R^{11}$ independently is H, OH, $NH_2$, or COOH.

6. A method comprising
(a) contacting a first fusion protein comprising an affinity reagent and a reactive enzyme comprising cutinase with a linker comprising a functional group specific for irreversibly inhibiting the first fusion protein reactive enzyme at a first terminus thereby coupling the first fusion protein reactive enzyme and the linker at the first terminus, and
(b) contacting a second fusion protein comprising an affinity reagent and a reactive enzyme comprising HaloTag or SnapTag with a second terminus of the linker, the second terminus of the linker comprising a functional group specific for irreversibly inhibiting the second fusion protein reactive enzyme thereby coupling the second fusion protein reactive enzyme and the linker at the second terminus,
thereby forming a construct comprising the first fusion protein coupled to the linker through the reactive enzyme of the first fusion protein and the functional group specific for irreversibly inhibiting the reactive enzyme of the first fusion protein and the second fusion protein coupled to the linker through the reactive enzyme of the second fusion protein and the functional group specific for irreversibly inhibiting the reactive enzyme of the second fusion protein;
wherein the first fusion protein affinity reagent and the second fusion protein affinity reagent each comprise an antibody or fragment thereof,
wherein the antibody fragment comprises Fab' fragments, F(ab)2 fragments, Fv fragments, Fc fragments, one or more complementarity determining regions (CDR) fragments, an individual heavy chain, an individual light chain, or a dimeric heavy and light chain.

7. The method of claim 6, wherein steps (a) and (b) are performed sequentially.

8. The method of claim 6, wherein steps (a) and (b) are preformed contemporaneously.

9. The method of claim 6, wherein the linker is a of polyoxazoline, polyacrylomorpholine, polyvinylpyrrolidone, polyphosphazene, polyethylene-co-maleic acid anhydride, polystyrene-co-maleic acid anhydride, poly(1-hydroxymethylethylene hydroxymethyl formal) ("PHF"), a polyhydroxyalkylacrylate, 2-methyacryloyloxy-2'-ethyltrimethylammonium phosphate ("MPC"), or a structure selected from:

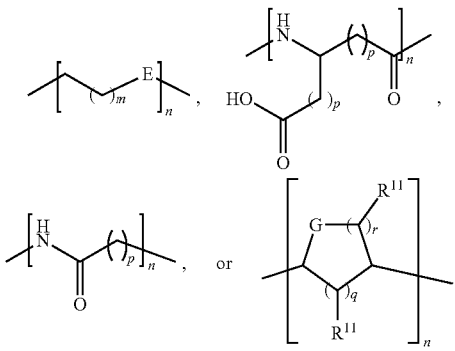

wherein:
m is 0-10;
n is 1-100;
each p independently is 0, 1, 2, 3, or 4;
q is 0, 1, or 2;
r is 1 or 2;
E is NH or $CHR^{10}$;
G is O, $CH_2$, CHOH, $CHNH_2$, CHCOOH, or $CHSO_3H$;
$R^{10}$ is OH, $NH_2$, or COOH;
each $R^{11}$ independently is H, OH, $NH_2$, or COOH.

10. A construct prepared by the method of claim 6.

11. A method comprising administering the construct of claim 1 to a patient in need thereof.

12. The method of claim 11, wherein the patient suffers from breast cancer, inhalational anthrax, rheumatoid arthritis, systemic juvenile idiopathic arthritis, Hodgkin lymphoma, systemic anaplastic large cell lymphoma, chronic lymphocytic leukemia, non-Hodgkin's lymphoma, diffuse large B cell lymphoma, multiple sclerosis, systemic lupus erythematosus, gastric or gastro-esophageal junction adenocarcinoma, metastatic non-small-cell lung carcinoma, ulcerative colitis, Crohn's disease, follicular lymphoma, melanoma, macular degeneration, osteoporosis, treatment-induced bone loss, metastases to bone, giant cell tumor of bone, malignant ascites, psoriatic arthritis, ankylosing spondylitis, metastatic renal cell cancer, prostate cancer, ovarian cancer, colorectal cancer, multiple myeloma, and Castleman's disease.

13. The construct of claim 1, wherein the antibody or fragment thereof is a chimeric antibody, a human antibody, or a humanized antibody.

14. The construct of claim 1, wherein the antibody or fragment thereof comprises trastuzumab or a fragment thereof.

15. The method of claim 6 wherein the antibody or fragment thereof is selected from the group consisting of a light chain variable domain ($V_L$), a light chain constant domain ($C_L$), a heavy chain variable domain ($V_H$), a heavy chain constant domain ($C_H1$), and a combination thereof.

16. The method of claim 6, wherein the antibody or fragment thereof is a chimeric antibody, a human antibody, or a humanized antibody.

17. The method of claim 6, wherein the antibody or fragment thereof comprises trastuzumab or a fragment thereof.

18. The method of claim 6, wherein the antibody or fragment thereof is selected from the group consisting of adalimumab, alemtuzumab, arcitumomab, cetuximab, trastuzumab, imciromab, capromab, infliximab, abciximab, rituximab, basiliximab, palivizumab, nofetumomab, omalizumab, daclizumab, ibritumomab tiuxetan, muromonab, edrecolomab gemtuzumab ozogamicin, golimumab, certolizumab, eculizumab, ustekinumab, panitumumab, tositumomab, bevacizumab, raxibacumab, tocilizumab, brentuximab, ofatumumab, belimumab, ramucirumab, vedolizumab, obinutuzumab, pembrolizumab, ranibizumab, pertuzumab, denosumab, catumaxomab, golimumab, siltuximab, natalizumab, panitumumab, and denosumab.

19. The method of claim 6, wherein the antibody or fragment thereof is a synthetic antibody domain.

* * * * *

UNITED STATES PATENT AND TRADEMARK OFFICE
CERTIFICATE OF CORRECTION

PATENT NO. : 12,098,215 B2  
APPLICATION NO. : 16/307621  
DATED : September 24, 2024  
INVENTOR(S) : Milan Mrksich et al.

Page 1 of 1

It is certified that error appears in the above-identified patent and that said Letters Patent is hereby corrected as shown below:

In the Claims

At Column 58, Line 61, "polyacrylomorpholine," should be -- polyacryloylmorpholine, --.

At Column 59, Line 27, "comprising" should be -- comprising: --.

At Column 59, Line 63, "preformed" should be -- performed --.

At Column 59, Line 65, "polyacrylomorpholine," should be -- polyacryloylmorpholine, --.

Signed and Sealed this  
Eighteenth Day of February, 2025

Coke Morgan Stewart  
*Acting Director of the United States Patent and Trademark Office*

SEQUENCE LISTING

<160> NUMBER OF SEQ ID NOS: 23

<210> SEQ ID NO 1
<211> LENGTH: 22
<212> TYPE: DNA
<213> ORGANISM: Artificial Sequence
<220> FEATURE:
<223> OTHER INFORMATION: Synthetic Polynucleotide

<400> SEQUENCE: 1
tttgcgtagt gtgtggtgct tt                                        22

<210> SEQ ID NO 2
<211> LENGTH: 22
<212> TYPE: DNA
<213> ORGANISM: Artificial Sequence
<220> FEATURE:
<223> OTHER INFORMATION: Synthetic Polynucleotide

<400> SEQUENCE: 2
tttgcgtggg gtgtggtgct tt                                        22

<210> SEQ ID NO 3

```
<211> LENGTH: 22
<212> TYPE: DNA
<213> ORGANISM: Artificial Sequence
<220> FEATURE:
<223> OTHER INFORMATION: Synthetic Polynucleotide

<400> SEQUENCE: 3
tttgcgtagg gtgtggtgct tt                                              22

<210> SEQ ID NO 4
<211> LENGTH: 44
<212> TYPE: DNA
<213> ORGANISM: Artificial Sequence
<220> FEATURE:
<223> OTHER INFORMATION: Synthetic Polynucleotide

<400> SEQUENCE: 4
cgcgcaccga aggtgcgta ttgtctatag cccagattta agga                       44

<210> SEQ ID NO 5
<211> LENGTH: 34
<212> TYPE: DNA
<213> ORGANISM: Artificial Sequence
<220> FEATURE:
<223> OTHER INFORMATION: Synthetic Polynucleotide

<400> SEQUENCE: 5
ccatttctcg aagagaaacc ggtaaatgcg ccct                                 34

<210> SEQ ID NO 6
<211> LENGTH: 39
<212> TYPE: DNA
<213> ORGANISM: Artificial Sequence
<220> FEATURE:
<223> OTHER INFORMATION: Synthetic Polynucleotide

<400> SEQUENCE: 6 cacacactt tatgaatataa agtatagtgt tatacttta                            39

<210> SEQ ID NO 7
<211> LENGTH: 40
<212> TYPE: DNA
<213> ORGANISM: Artificial Sequence
<220> FEATURE:
<223> OTHER INFORMATION: Synthetic Polynucleotide

<400> SEQUENCE: 7
acgtttctga acgaagtgaa gaaacgtcta agtgcgccct                           40

<210> SEQ ID NO 8
<211> LENGTH: 440
<212> TYPE: PRT
<213> ORGANISM: Artificial Sequence
<220> FEATURE:
<223> OTHER INFORMATION: Synthetic Polypeptide

<400> SEQUENCE: 8

Met Gly Leu Pro Thr Ser Asn Pro Ala Gln Glu Leu Glu Ala Arg Gln
1               5                   10                  15

Leu Gly Arg Thr Thr Arg Asp Asp Leu Ile Asn Gly Asn Ser Ala Ser
            20                  25                  30

Cys Ala Asp Val Ile Phe Ile Tyr Ala Arg Gly Ser Thr Glu Thr Gly
        35                  40                  45

Asn Leu Gly Thr Leu Gly Pro Ser Ile Ala Ser Asn Leu Glu Ser Ala
    50                  55                  60
```

```
Phe Gly Lys Asp Gly Val Trp Ile Gln Gly Val Gly Ala Tyr Arg
 65                  70                  75                  80

Ala Thr Leu Gly Asp Asn Ala Leu Pro Arg Gly Thr Ser Ser Ala Ala
                 85                  90                  95

Ile Arg Glu Met Leu Gly Leu Phe Gln Gln Ala Asn Thr Lys Cys Pro
            100                 105                 110

Asp Ala Thr Leu Ile Ala Gly Gly Tyr Ser Gln Gly Ala Ala Leu Ala
        115                 120                 125

Ala Ala Ser Ile Glu Asp Leu Asp Ser Ala Ile Arg Asp Lys Ile Ala
130                 135                 140

Gly Thr Val Leu Phe Gly Tyr Thr Lys Asn Leu Gln Asn Arg Gly Arg
145                 150                 155                 160

Ile Pro Asn Tyr Pro Ala Asp Arg Thr Lys Val Phe Cys Asn Thr Gly
                165                 170                 175

Asp Leu Val Cys Thr Gly Ser Leu Ile Val Ala Ala Pro His Leu Ala
            180                 185                 190

Tyr Gly Pro Asp Ala Arg Gly Pro Ala Pro Glu Phe Leu Ile Glu Lys
        195                 200                 205

Val Arg Ala Val Arg Gly Ser Ala Glu Ala Ala Lys Glu Ala Ala
210                 215                 220

Ala Lys Asp Ile Gln Met Thr Gln Ser Pro Ser Ser Leu Ser Ala Ser
225                 230                 235                 240

Val Gly Asp Arg Val Thr Ile Thr Cys Arg Ala Ser Gln Asp Val Asn
                245                 250                 255

Thr Ala Val Ala Trp Tyr Gln Gln Lys Pro Gly Lys Ala Pro Lys Leu
            260                 265                 270

Leu Ile Tyr Ser Ala Ser Phe Leu Tyr Ser Gly Val Pro Ser Arg Phe
        275                 280                 285

Ser Gly Ser Arg Ser Gly Thr Asp Phe Thr Leu Thr Ile Ser Ser Leu
290                 295                 300

Gln Pro Glu Asp Phe Ala Thr Tyr Tyr Cys Gln Gln His Tyr Thr Thr
305                 310                 315                 320

Pro Pro Thr Phe Gly Gln Gly Thr Lys Val Glu Ile Lys Arg Thr Val
                325                 330                 335

Ala Ala Pro Ser Val Phe Ile Phe Pro Pro Ser Asp Glu Gln Leu Lys
            340                 345                 350

Ser Gly Thr Ala Ser Val Val Cys Leu Leu Asn Asn Phe Tyr Pro Arg
        355                 360                 365

Glu Ala Lys Val Gln Trp Lys Val Asp Asn Ala Leu Gln Ser Gly Asn
370                 375                 380

Ser Gln Glu Ser Val Thr Glu Gln Asp Ser Lys Asp Ser Thr Tyr Ser
385                 390                 395                 400

Leu Ser Ser Thr Leu Thr Leu Ser Lys Ala Asp Tyr Glu Lys His Lys
                405                 410                 415

Val Tyr Ala Cys Glu Val Thr His Gln Gly Leu Ser Ser Pro Val Thr
            420                 425                 430

Lys Ser Phe Asn Arg Gly Glu Cys
        435                 440

<210> SEQ ID NO 9
<211> LENGTH: 236
<212> TYPE: PRT
<213> ORGANISM: Artificial Sequence
<220> FEATURE:
```

<223> OTHER INFORMATION: Synthetic Polypeptide

<400> SEQUENCE: 9

Met Glu Val Gln Leu Val Glu Ser Gly Gly Gly Leu Val Gln Pro Gly
1               5                   10                  15

Gly Ser Leu Arg Leu Ser Cys Ala Ala Ser Gly Phe Asn Ile Lys Asp
            20                  25                  30

Thr Tyr Ile His Trp Val Arg Gln Ala Pro Gly Lys Gly Leu Glu Trp
        35                  40                  45

Val Ala Arg Ile Tyr Pro Thr Asn Gly Tyr Thr Arg Tyr Ala Asp Ser
    50                  55                  60

Val Lys Gly Arg Phe Thr Ile Ser Ala Asp Thr Ser Lys Asn Thr Ala
65                  70                  75                  80

Tyr Leu Gln Met Asn Ser Leu Arg Ala Glu Asp Thr Ala Val Tyr Tyr
                85                  90                  95

Cys Ser Arg Trp Gly Gly Asp Gly Phe Tyr Ala Met Asp Tyr Trp Gly
            100                 105                 110

Gln Gly Thr Leu Val Thr Val Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Leu Val Pro Arg Gly Ser His His His His His
225                 230                 235

<210> SEQ ID NO 10
<211> LENGTH: 406
<212> TYPE: PRT
<213> ORGANISM: Artificial Sequence
<220> FEATURE:
<223> OTHER INFORMATION: Synthetic Polypeptide

<400> SEQUENCE: 10

Met Asp Lys Asp Cys Glu Met Lys Arg Thr Thr Leu Asp Ser Pro Leu
1               5                   10                  15

Gly Lys Leu Glu Leu Ser Gly Cys Glu Gln Gly Leu His Glu Ile Ile
            20                  25                  30

Phe Leu Gly Lys Gly Thr Ser Ala Ala Asp Ala Val Glu Val Pro Ala
        35                  40                  45

Pro Ala Ala Val Leu Gly Gly Pro Glu Pro Leu Met Gln Ala Thr Ala
    50                  55                  60

Trp Leu Asn Ala Tyr Phe His Gln Pro Glu Ala Ile Glu Glu Phe Pro
65                  70                  75                  80

Val Pro Ala Leu His His Pro Val Phe Gln Gln Glu Ser Phe Thr Arg
                85                  90                  95

Gln Val Leu Trp Lys Leu Leu Lys Val Val Lys Phe Gly Glu Val Ile
            100                 105                 110

Ser Tyr Ser His Leu Ala Ala Leu Ala Gly Asn Pro Ala Ala Thr Ala
            115                 120                 125

Ala Val Lys Thr Ala Leu Ser Gly Asn Pro Val Pro Ile Leu Ile Pro
130                 135                 140

Cys His Arg Val Val Gln Gly Asp Leu Asp Val Gly Gly Tyr Glu Gly
145                 150                 155                 160

Gly Leu Ala Val Lys Glu Trp Leu Leu Ala His Glu Gly His Arg Leu
                165                 170                 175

Gly Lys Pro Gly Leu Gly Glu Ala Ala Lys Glu Ala Ala Ala Lys
            180                 185                 190

Asp Ile Gln Met Thr Gln Ser Pro Ser Ser Leu Ser Ala Ser Val Gly
            195                 200                 205

Asp Arg Val Thr Ile Thr Cys Arg Ala Ser Gln Asp Val Asn Thr Ala
            210                 215                 220

Val Ala Trp Tyr Gln Gln Lys Pro Gly Lys Ala Pro Lys Leu Leu Ile
225                 230                 235                 240

Tyr Ser Ala Ser Phe Leu Tyr Ser Gly Val Pro Ser Arg Phe Ser Gly
                245                 250                 255

Ser Arg Ser Gly Thr Asp Phe Thr Leu Thr Ile Ser Ser Leu Gln Pro
            260                 265                 270

Glu Asp Phe Ala Thr Tyr Tyr Cys Gln Gln His Tyr Thr Thr Pro Pro
            275                 280                 285

Thr Phe Gly Gln Gly Thr Lys Val Glu Ile Lys Arg Thr Val Ala Ala
            290                 295                 300

Pro Ser Val Phe Ile Phe Pro Pro Ser Asp Glu Gln Leu Lys Ser Gly
305                 310                 315                 320

Thr Ala Ser Val Val Cys Leu Leu Asn Asn Phe Tyr Pro Arg Glu Ala
                325                 330                 335

Lys Val Gln Trp Lys Val Asp Asn Ala Leu Gln Ser Gly Asn Ser Gln
            340                 345                 350

Glu Ser Val Thr Glu Gln Asp Ser Lys Asp Ser Thr Tyr Ser Leu Ser
            355                 360                 365

Ser Thr Leu Thr Leu Ser Lys Ala Asp Tyr Glu Lys His Lys Val Tyr
            370                 375                 380

Ala Cys Glu Val Thr His Gln Gly Leu Ser Ser Pro Val Thr Lys Ser
385                 390                 395                 400

Phe Asn Arg Gly Glu Cys
                405

<210> SEQ ID NO 11
<211> LENGTH: 236
<212> TYPE: PRT
<213> ORGANISM: Artificial Sequence
<220> FEATURE:
<223> OTHER INFORMATION: Synthetic Polypeptide

<400> SEQUENCE: 11

Met Glu Val Gln Leu Val Glu Ser Gly Gly Gly Leu Val Gln Pro Gly
1               5                   10                  15

Gly Ser Leu Arg Leu Ser Cys Ala Ala Ser Gly Phe Asn Ile Lys Asp
            20                  25                  30

Thr Tyr Ile His Trp Val Arg Gln Ala Pro Gly Lys Gly Leu Glu Trp
        35                  40                  45

Val Ala Arg Ile Tyr Pro Thr Asn Gly Tyr Thr Arg Tyr Ala Asp Ser
    50                  55                  60

Val Lys Gly Arg Phe Thr Ile Ser Ala Asp Thr Ser Lys Asn Thr Ala
65                  70                  75                  80

Tyr Leu Gln Met Asn Ser Leu Arg Ala Glu Asp Thr Ala Val Tyr Tyr
                85                  90                  95

Cys Ser Arg Trp Gly Asp Gly Phe Tyr Ala Met Asp Tyr Trp Gly
            100                 105                 110

Gln Gly Thr Leu Val Thr Val Ser Ser Ala Ser Thr Lys Gly Pro Ser
            115                 120                 125

Val Phe Pro Leu Ala Pro Ser Ser Lys Ser Thr Ser Gly Gly Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
            195                 200                 205

Lys Pro Ser Asn Thr Lys Val Asp Lys Lys Val Glu Pro Lys Ser Cys
210                 215                 220

Leu Val Pro Arg Gly Ser His His His His His His
225                 230                 235

<210> SEQ ID NO 12
<211> LENGTH: 440
<212> TYPE: PRT
<213> ORGANISM: Artificial Sequence
<220> FEATURE:
<223> OTHER INFORMATION: Synthetic Polypeptide

<400> SEQUENCE: 12

Met Asp Ile Gln Met Thr Gln Ser Pro Ser Ser Leu Ser Ala Ser Val
1               5                   10                  15

Gly Asp Arg Val Thr Ile Thr Cys Arg Ala Ser Gln Asp Val Asn Thr
            20                  25                  30

Ala Val Ala Trp Tyr Gln Gln Lys Pro Gly Lys Ala Pro Lys Leu Leu
        35                  40                  45

Ile Tyr Ser Ala Ser Phe Leu Tyr Ser Gly Val Pro Ser Arg Phe Ser
    50                  55                  60

Gly Ser Arg Ser Gly Thr Asp Phe Thr Leu Thr Ile Ser Ser Leu Gln
65                  70                  75                  80

Pro Glu Asp Phe Ala Thr Tyr Tyr Cys Gln Gln His Tyr Thr Thr Pro
                85                  90                  95

Pro Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
            115                 120                 125

Gly Thr Ala Ser Val Val Cys Leu Leu Asn Asn Phe Tyr Pro Arg Glu
130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
            195                 200                 205

Ser Phe Asn Arg Gly Glu Cys Glu Ala Ala Lys Glu Ala Ala Ala
    210                 215                 220

Lys Gly Leu Pro Thr Ser Asn Pro Ala Gln Glu Leu Glu Ala Arg Gln
225                 230                 235                 240

Leu Gly Arg Thr Thr Arg Asp Asp Leu Ile Asn Gly Asn Ser Ala Ser
                245                 250                 255

Cys Ala Asp Val Ile Phe Ile Tyr Ala Arg Gly Ser Thr Glu Thr Gly
                260                 265                 270

Asn Leu Gly Thr Leu Gly Pro Ser Ile Ala Ser Asn Leu Glu Ser Ala
            275                 280                 285

Phe Gly Lys Asp Gly Val Trp Ile Gln Gly Val Gly Gly Ala Tyr Arg
    290                 295                 300

Ala Thr Leu Gly Asp Asn Ala Leu Pro Arg Gly Thr Ser Ser Ala Ala
305                 310                 315                 320

Ile Arg Glu Met Leu Gly Leu Phe Gln Gln Ala Asn Thr Lys Cys Pro
                325                 330                 335

Asp Ala Thr Leu Ile Ala Gly Gly Tyr Ser Gln Gly Ala Ala Leu Ala
                340                 345                 350

Ala Ala Ser Ile Glu Asp Leu Asp Ser Ala Ile Arg Asp Lys Ile Ala
            355                 360                 365

Gly Thr Val Leu Phe Gly Tyr Thr Lys Asn Leu Gln Asn Arg Gly Arg
    370                 375                 380

Ile Pro Asn Tyr Pro Ala Asp Arg Thr Lys Val Phe Cys Asn Thr Gly
385                 390                 395                 400

Asp Leu Val Cys Thr Gly Ser Leu Ile Val Ala Ala Pro His Leu Ala
                405                 410                 415

Tyr Gly Pro Asp Ala Arg Gly Pro Ala Pro Glu Phe Leu Ile Glu Lys
                420                 425                 430

Val Arg Ala Val Arg Gly Ser Ala
            435                 440

<210> SEQ ID NO 13
<211> LENGTH: 236
<212> TYPE: PRT
<213> ORGANISM: Artificial Sequence
<220> FEATURE:
<223> OTHER INFORMATION: Synthetic Polypeptide

<400> SEQUENCE: 13

Met Glu Val Gln Leu Val Glu Ser Gly Gly Gly Leu Val Gln Pro Gly
1               5                   10                  15

Gly Ser Leu Arg Leu Ser Cys Ala Ala Ser Gly Phe Asn Ile Lys Asp
            20                  25                  30

Thr Tyr Ile His Trp Val Arg Gln Ala Pro Gly Lys Gly Leu Glu Trp
        35                  40                  45

Val Ala Arg Ile Tyr Pro Thr Asn Gly Tyr Thr Arg Tyr Ala Asp Ser
    50                  55                  60

Val Lys Gly Arg Phe Thr Ile Ser Ala Asp Thr Ser Lys Asn Thr Ala
65                  70                  75                  80

Tyr Leu Gln Met Asn Ser Leu Arg Ala Glu Asp Thr Ala Val Tyr Tyr
                85                  90                  95

Cys Ser Arg Trp Gly Gly Asp Gly Phe Tyr Ala Met Asp Tyr Trp Gly
                100                 105                 110

Gln Gly Thr Leu Val Thr Val Ser Ser Ala Ser Thr Lys Gly Pro Ser
    115                 120                 125

Val Phe Pro Leu Ala Pro Ser Ser Lys Ser Thr Ser Gly Gly Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Leu Val Pro Arg Gly Ser His His His His His
225                 230                 235

<210> SEQ ID NO 14
<211> LENGTH: 406
<212> TYPE: PRT
<213> ORGANISM: Artificial Sequence
<220> FEATURE:
<223> OTHER INFORMATION: Synthetic Polypeptide

<400> SEQUENCE: 14

Met Asp Ile Gln Met Thr Gln Ser Pro Ser Ser Leu Ser Ala Ser Val
1               5                   10                  15

Gly Asp Arg Val Thr Ile Thr Cys Arg Ala Ser Gln Asp Val Asn Thr
            20                  25                  30

Ala Val Ala Trp Tyr Gln Gln Lys Pro Gly Lys Ala Pro Lys Leu Leu
        35                  40                  45

Ile Tyr Ser Ala Ser Phe Leu Tyr Ser Gly Val Pro Ser Arg Phe Ser
    50                  55                  60

Gly Ser Arg Ser Gly Thr Asp Phe Thr Leu Thr Ile Ser Ser Leu Gln
65                  70                  75                  80

Pro Glu Asp Phe Ala Thr Tyr Tyr Cys Gln Gln His Tyr Thr Thr Pro
                85                  90                  95

Pro Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys Glu Ala Ala Lys Glu Ala Ala Ala
    210                 215                 220

Lys Asp Lys Asp Cys Glu Met Lys Arg Thr Thr Leu Asp Ser Pro Leu
225                 230                 235                 240

```
Gly Lys Leu Glu Leu Ser Gly Cys Glu Gln Gly Leu His Glu Ile Ile
                245                 250                 255

Phe Leu Gly Lys Gly Thr Ser Ala Ala Asp Ala Val Glu Val Pro Ala
            260                 265                 270

Pro Ala Val Leu Gly Gly Pro Glu Pro Leu Met Gln Ala Thr Ala
        275                 280                 285

Trp Leu Asn Ala Tyr Phe His Gln Pro Glu Ala Ile Glu Glu Phe Pro
    290                 295                 300

Val Pro Ala Leu His His Pro Val Phe Gln Gln Ser Phe Thr Arg
305                 310                 315                 320

Gln Val Leu Trp Lys Leu Leu Lys Val Val Lys Phe Gly Glu Val Ile
                325                 330                 335

Ser Tyr Ser His Leu Ala Ala Leu Ala Gly Asn Pro Ala Ala Thr Ala
                340                 345                 350

Ala Val Lys Thr Ala Leu Ser Gly Asn Pro Val Pro Ile Leu Ile Pro
            355                 360                 365

Cys His Arg Val Val Gln Gly Asp Leu Asp Val Gly Gly Tyr Glu Gly
        370                 375                 380

Gly Leu Ala Val Lys Glu Trp Leu Leu Ala His Glu Gly His Arg Leu
385                 390                 395                 400

Gly Lys Pro Gly Leu Gly
                405

<210> SEQ ID NO 15
<211> LENGTH: 236
<212> TYPE: PRT
<213> ORGANISM: Artificial Sequence
<220> FEATURE:
<223> OTHER INFORMATION: Synthetic Polypeptide

<400> SEQUENCE: 15

Met Glu Val Gln Leu Val Glu Ser Gly Gly Gly Leu Val Gln Pro Gly
1               5                   10                  15

Gly Ser Leu Arg Leu Ser Cys Ala Ala Ser Gly Phe Asn Ile Lys Asp
            20                  25                  30

Thr Tyr Ile His Trp Val Arg Gln Ala Pro Gly Lys Gly Leu Glu Trp
        35                  40                  45

Val Ala Arg Ile Tyr Pro Thr Asn Gly Tyr Thr Arg Tyr Ala Asp Ser
    50                  55                  60

Val Lys Gly Arg Phe Thr Ile Ser Ala Asp Thr Ser Lys Asn Thr Ala
65                  70                  75                  80

Tyr Leu Gln Met Asn Ser Leu Arg Ala Glu Asp Thr Ala Val Tyr Tyr
                85                  90                  95

Cys Ser Arg Trp Gly Gly Asp Gly Phe Tyr Ala Met Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190
```

```
Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Leu Val Pro Arg Gly Ser His His His His His His
225                 230                 235

<210> SEQ ID NO 16
<211> LENGTH: 215
<212> TYPE: PRT
<213> ORGANISM: Artificial Sequence
<220> FEATURE:
<223> OTHER INFORMATION: Synthetic Polypeptide

<400> SEQUENCE: 16

Met Asp Ile Gln Met Thr Gln Ser Pro Ser Ser Leu Ser Ala Ser Val
1               5                   10                  15

Gly Asp Arg Val Thr Ile Thr Cys Arg Ala Ser Gln Asp Val Asn Thr
            20                  25                  30

Ala Val Ala Trp Tyr Gln Gln Lys Pro Gly Lys Ala Pro Lys Leu Leu
        35                  40                  45

Ile Tyr Ser Ala Ser Phe Leu Tyr Ser Gly Val Pro Ser Arg Phe Ser
    50                  55                  60

Gly Ser Arg Ser Gly Thr Asp Phe Thr Leu Thr Ile Ser Ser Leu Gln
65                  70                  75                  80

Pro Glu Asp Phe Ala Thr Tyr Tyr Cys Gln Gln His Tyr Thr Thr Pro
                85                  90                  95

Pro Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 17
<211> LENGTH: 461
<212> TYPE: PRT
<213> ORGANISM: Artificial Sequence
<220> FEATURE:
<223> OTHER INFORMATION: Synthetic Polypeptide

<400> SEQUENCE: 17

Met Gly Leu Pro Thr Ser Asn Pro Ala Gln Glu Leu Glu Ala Arg Gln
1               5                   10                  15

Leu Gly Arg Thr Thr Arg Asp Asp Leu Ile Asn Gly Asn Ser Ala Ser
            20                  25                  30

Cys Ala Asp Val Ile Phe Ile Tyr Ala Arg Gly Ser Thr Glu Thr Gly
```

```
                    35                  40                  45
Asn Leu Gly Thr Leu Gly Pro Ser Ile Ala Ser Asn Leu Glu Ser Ala
 50                  55                  60

Phe Gly Lys Asp Gly Val Trp Ile Gln Gly Val Gly Ala Tyr Arg
 65                  70                  75                  80

Ala Thr Leu Gly Asp Asn Ala Leu Pro Arg Gly Thr Ser Ser Ala Ala
                 85                  90                  95

Ile Arg Glu Met Leu Gly Leu Phe Gln Gln Ala Asn Thr Lys Cys Pro
                100                 105                 110

Asp Ala Thr Leu Ile Ala Gly Tyr Ser Gln Gly Ala Ala Leu Ala
                115                 120                 125

Ala Ala Ser Ile Glu Asp Leu Asp Ser Ala Ile Arg Asp Lys Ile Ala
130                 135                 140

Gly Thr Val Leu Phe Gly Tyr Thr Lys Asn Leu Gln Asn Arg Gly Arg
145                 150                 155                 160

Ile Pro Asn Tyr Pro Ala Asp Arg Thr Lys Val Phe Cys Asn Thr Gly
                165                 170                 175

Asp Leu Val Cys Thr Gly Ser Leu Ile Val Ala Ala Pro His Leu Ala
                180                 185                 190

Tyr Gly Pro Asp Ala Arg Gly Pro Ala Pro Glu Phe Leu Ile Glu Lys
                195                 200                 205

Val Arg Ala Val Arg Gly Ser Ala Glu Ala Ala Ala Lys Glu Ala Ala
210                 215                 220

Ala Lys Glu Val Gln Leu Val Glu Ser Gly Gly Gly Leu Val Gln Pro
225                 230                 235                 240

Gly Gly Ser Leu Arg Leu Ser Cys Ala Ala Ser Gly Phe Asn Ile Lys
                245                 250                 255

Asp Thr Tyr Ile His Trp Val Arg Gln Ala Pro Gly Lys Gly Leu Glu
                260                 265                 270

Trp Val Ala Arg Ile Tyr Pro Thr Asn Gly Tyr Thr Arg Tyr Ala Asp
                275                 280                 285

Ser Val Lys Gly Arg Phe Thr Ile Ser Ala Asp Thr Ser Lys Asn Thr
290                 295                 300

Ala Tyr Leu Gln Met Asn Ser Leu Arg Ala Glu Asp Thr Ala Val Tyr
305                 310                 315                 320

Tyr Cys Ser Arg Trp Gly Gly Asp Gly Phe Tyr Ala Met Asp Tyr Trp
                325                 330                 335

Gly Gln Gly Thr Leu Val Thr Val Ser Ser Ala Ser Thr Lys Gly Pro
                340                 345                 350

Ser Val Phe Pro Leu Ala Pro Ser Ser Lys Ser Thr Ser Gly Gly Thr
                355                 360                 365

Ala Ala Leu Gly Cys Leu Val Lys Asp Tyr Phe Pro Glu Pro Val Thr
                370                 375                 380

Val Ser Trp Asn Ser Gly Ala Leu Thr Ser Gly Val His Thr Phe Pro
385                 390                 395                 400

Ala Val Leu Gln Ser Ser Gly Leu Tyr Ser Leu Ser Ser Val Val Thr
                405                 410                 415

Val Pro Ser Ser Ser Leu Gly Thr Gln Thr Tyr Ile Cys Asn Val Asn
                420                 425                 430

His Lys Pro Ser Asn Thr Lys Val Asp Lys Lys Val Glu Pro Lys Ser
                435                 440                 445

Cys Leu Val Pro Arg Gly Ser His His His His His
                450                 455                 460
```

<210> SEQ ID NO 18
<211> LENGTH: 215
<212> TYPE: PRT
<213> ORGANISM: Artificial Sequence
<220> FEATURE:
<223> OTHER INFORMATION: Synthetic Polypeptide

<400> SEQUENCE: 18

```
Met Asp Ile Gln Met Thr Gln Ser Pro Ser Ser Leu Ser Ala Ser Val
1               5                   10                  15

Gly Asp Arg Val Thr Ile Thr Cys Arg Ala Ser Gln Asp Val Asn Thr
            20                  25                  30

Ala Val Ala Trp Tyr Gln Gln Lys Pro Gly Lys Ala Pro Lys Leu Leu
        35                  40                  45

Ile Tyr Ser Ala Ser Phe Leu Tyr Ser Gly Val Pro Ser Arg Phe Ser
    50                  55                  60

Gly Ser Arg Ser Gly Thr Asp Phe Thr Leu Thr Ile Ser Ser Leu Gln
65                  70                  75                  80

Pro Glu Asp Phe Ala Thr Tyr Tyr Cys Gln Gln His Tyr Thr Thr Pro
                85                  90                  95

Pro Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215
```

<210> SEQ ID NO 19
<211> LENGTH: 427
<212> TYPE: PRT
<213> ORGANISM: Artificial Sequence
<220> FEATURE:
<223> OTHER INFORMATION: Synthetic Polypeptide

<400> SEQUENCE: 19

```
Met Asp Lys Asp Cys Glu Met Lys Arg Thr Thr Leu Asp Ser Pro Leu
1               5                   10                  15

Gly Lys Leu Glu Leu Ser Gly Cys Glu Gln Gly Leu His Glu Ile Ile
            20                  25                  30

Phe Leu Gly Lys Gly Thr Ser Ala Ala Asp Ala Val Glu Val Pro Ala
        35                  40                  45

Pro Ala Ala Val Leu Gly Gly Pro Glu Pro Leu Met Gln Ala Thr Ala
    50                  55                  60

Trp Leu Asn Ala Tyr Phe His Gln Pro Glu Ala Ile Glu Glu Phe Pro
65                  70                  75                  80

Val Pro Ala Leu His His Pro Val Phe Gln Gln Glu Ser Phe Thr Arg
```

```
            85                  90                  95
Gln Val Leu Trp Lys Leu Leu Lys Val Val Lys Phe Gly Glu Val Ile
            100                 105                 110
Ser Tyr Ser His Leu Ala Ala Leu Ala Gly Asn Pro Ala Ala Thr Ala
            115                 120                 125
Ala Val Lys Thr Ala Leu Ser Gly Asn Pro Val Pro Ile Leu Ile Pro
        130                 135                 140
Cys His Arg Val Val Gln Gly Asp Leu Asp Val Gly Gly Tyr Glu Gly
145                 150                 155                 160
Gly Leu Ala Val Lys Glu Trp Leu Leu Ala His Glu Gly His Arg Leu
                165                 170                 175
Gly Lys Pro Gly Leu Gly Glu Ala Ala Lys Glu Ala Ala Lys
            180                 185                 190
Glu Val Gln Leu Val Glu Ser Gly Gly Gly Leu Val Gln Pro Gly Gly
            195                 200                 205
Ser Leu Arg Leu Ser Cys Ala Ala Ser Gly Phe Asn Ile Lys Asp Thr
        210                 215                 220
Tyr Ile His Trp Val Arg Gln Ala Pro Gly Lys Gly Leu Glu Trp Val
225                 230                 235                 240
Ala Arg Ile Tyr Pro Thr Asn Gly Tyr Thr Arg Tyr Ala Asp Ser Val
                245                 250                 255
Lys Gly Arg Phe Thr Ile Ser Ala Asp Thr Ser Lys Asn Thr Ala Tyr
            260                 265                 270
Leu Gln Met Asn Ser Leu Arg Ala Glu Asp Thr Ala Val Tyr Tyr Cys
            275                 280                 285
Ser Arg Trp Gly Gly Asp Gly Phe Tyr Ala Met Asp Tyr Trp Gly Gln
        290                 295                 300
Gly Thr Leu Val Thr Val Ser Ser Ala Ser Thr Lys Gly Pro Ser Val
305                 310                 315                 320
Phe Pro Leu Ala Pro Ser Ser Lys Ser Thr Ser Gly Gly Thr Ala Ala
                325                 330                 335
Leu Gly Cys Leu Val Lys Asp Tyr Phe Pro Glu Pro Val Thr Val Ser
            340                 345                 350
Trp Asn Ser Gly Ala Leu Thr Ser Gly Val His Thr Phe Pro Ala Val
            355                 360                 365
Leu Gln Ser Ser Gly Leu Tyr Ser Leu Ser Ser Val Val Thr Val Pro
        370                 375                 380
Ser Ser Ser Leu Gly Thr Gln Thr Tyr Ile Cys Asn Val Asn His Lys
385                 390                 395                 400
Pro Ser Asn Thr Lys Val Asp Lys Lys Val Glu Pro Lys Ser Cys Leu
                405                 410                 415
Val Pro Arg Gly Ser His His His His His
            420                 425

<210> SEQ ID NO 20
<211> LENGTH: 215
<212> TYPE: PRT
<213> ORGANISM: Artificial Sequence
<220> FEATURE:
<223> OTHER INFORMATION: Synthetic Polypeptide

<400> SEQUENCE: 20

Met Asp Ile Gln Met Thr Gln Ser Pro Ser Ser Leu Ser Ala Ser Val
1               5                   10                  15

Gly Asp Arg Val Thr Ile Thr Cys Arg Ala Ser Gln Asp Val Asn Thr
```

```
              20                  25                  30
Ala Val Ala Trp Tyr Gln Gln Lys Pro Gly Lys Ala Pro Lys Leu Leu
            35                  40                  45

Ile Tyr Ser Ala Ser Phe Leu Tyr Ser Gly Val Pro Ser Arg Phe Ser
        50                  55                  60

Gly Ser Arg Ser Gly Thr Asp Phe Thr Leu Thr Ile Ser Ser Leu Gln
65                  70                  75                  80

Pro Glu Asp Phe Ala Thr Tyr Tyr Cys Gln Gln His Tyr Thr Thr Pro
                85                  90                  95

Pro Thr Phe Gly Gln Gly Thr Lys Val Glu Ile Lys Arg Thr Val Ala
                100                 105                 110

Ala Pro Ser Val Phe Ile Phe Pro Pro Ser Asp Glu Gln Leu Lys Ser
            115                 120                 125

Gly Thr Ala Ser Val Val Cys Leu Leu Asn Asn Phe Tyr Pro Arg Glu
        130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
                180                 185                 190

Tyr Ala Cys Glu Val Thr His Gln Gly Leu Ser Ser Pro Val Thr Lys
            195                 200                 205

Ser Phe Asn Arg Gly Glu Cys
        210                 215

<210> SEQ ID NO 21
<211> LENGTH: 461
<212> TYPE: PRT
<213> ORGANISM: Artificial Sequence
<220> FEATURE:
<223> OTHER INFORMATION: Synthetic Polypeptide

<400> SEQUENCE: 21

Met Glu Val Gln Leu Val Glu Ser Gly Gly Gly Leu Val Gln Pro Gly
1               5                   10                  15

Gly Ser Leu Arg Leu Ser Cys Ala Ala Ser Gly Phe Asn Ile Lys Asp
            20                  25                  30

Thr Tyr Ile His Trp Val Arg Gln Ala Pro Gly Lys Gly Leu Glu Trp
        35                  40                  45

Val Ala Arg Ile Tyr Pro Thr Asn Gly Tyr Thr Arg Tyr Ala Asp Ser
    50                  55                  60

Val Lys Gly Arg Phe Thr Ile Ser Ala Asp Thr Ser Lys Asn Thr Ala
65                  70                  75                  80

Tyr Leu Gln Met Asn Ser Leu Arg Ala Glu Asp Thr Ala Val Tyr Tyr
                85                  90                  95

Cys Ser Arg Trp Gly Gly Asp Gly Phe Tyr Ala Met Asp Tyr Trp Gly
                100                 105                 110

Gln Gly Thr Leu Val Thr Val Ser Ser Ala Ser Thr Lys Gly Pro Ser
            115                 120                 125

Val Phe Pro Leu Ala Pro Ser Ser Lys Ser Thr Ser Gly Gly Thr Ala
        130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
```

```
                    165                 170                 175
Val Leu Gln Ser Ser Gly Leu Tyr Ser Leu Ser Ser Val Val Thr Val
                180                 185                 190

Pro Ser Ser Ser Leu Gly Thr Gln Thr Tyr Ile Cys Asn Val Asn His
            195                 200                 205

Lys Pro Ser Asn Thr Lys Val Asp Lys Val Glu Pro Lys Ser Cys
    210                 215                 220

Glu Ala Ala Lys Glu Ala Ala Lys Gly Leu Pro Thr Ser Asn
225                 230                 235                 240

Pro Ala Gln Glu Leu Glu Ala Arg Gln Leu Gly Arg Thr Thr Arg Asp
                245                 250                 255

Asp Leu Ile Asn Gly Asn Ser Ala Ser Cys Ala Asp Val Ile Phe Ile
                260                 265                 270

Tyr Ala Arg Gly Ser Thr Glu Thr Gly Asn Leu Gly Thr Leu Gly Pro
            275                 280                 285

Ser Ile Ala Ser Asn Leu Glu Ser Ala Phe Gly Lys Asp Gly Val Trp
        290                 295                 300

Ile Gln Gly Val Gly Gly Ala Tyr Arg Ala Thr Leu Gly Asp Asn Ala
305                 310                 315                 320

Leu Pro Arg Gly Thr Ser Ser Ala Ala Ile Arg Glu Met Leu Gly Leu
                325                 330                 335

Phe Gln Gln Ala Asn Thr Lys Cys Pro Asp Ala Thr Leu Ile Ala Gly
                340                 345                 350

Gly Tyr Ser Gln Gly Ala Ala Leu Ala Ala Ser Ile Glu Asp Leu
            355                 360                 365

Asp Ser Ala Ile Arg Asp Lys Ile Ala Gly Thr Val Leu Phe Gly Tyr
        370                 375                 380

Thr Lys Asn Leu Gln Asn Arg Gly Arg Ile Pro Asn Tyr Pro Ala Asp
385                 390                 395                 400

Arg Thr Lys Val Phe Cys Asn Thr Gly Asp Leu Val Cys Thr Gly Ser
                405                 410                 415

Leu Ile Val Ala Ala Pro His Leu Ala Tyr Gly Pro Asp Ala Arg Gly
                420                 425                 430

Pro Ala Pro Glu Phe Leu Ile Glu Lys Val Arg Ala Val Arg Gly Ser
            435                 440                 445

Ala Leu Val Pro Arg Gly Ser His His His His His His
        450                 455                 460

<210> SEQ ID NO 22
<211> LENGTH: 215
<212> TYPE: PRT
<213> ORGANISM: Artificial Sequence
<220> FEATURE:
<223> OTHER INFORMATION: Synthetic Polypeptide

<400> SEQUENCE: 22

Met Asp Ile Gln Met Thr Gln Ser Pro Ser Ser Leu Ser Ala Ser Val
1               5                   10                  15

Gly Asp Arg Val Thr Ile Thr Cys Arg Ala Ser Gln Asp Val Asn Thr
            20                  25                  30

Ala Val Ala Trp Tyr Gln Gln Lys Pro Gly Lys Ala Pro Lys Leu Leu
        35                  40                  45

Ile Tyr Ser Ala Ser Phe Leu Tyr Ser Gly Val Pro Ser Arg Phe Ser
    50                  55                  60

Gly Ser Arg Ser Gly Thr Asp Phe Thr Leu Thr Ile Ser Ser Leu Gln
```

```
                65                  70                  75                  80
Pro Glu Asp Phe Ala Thr Tyr Tyr Cys Gln Gln His Tyr Thr Thr Pro
                    85                  90                  95

Pro Thr Phe Gly Gln Gly Thr Lys Val Glu Ile Lys Arg Thr Val Ala
                100                 105                 110

Ala Pro Ser Val Phe Ile Phe Pro Ser Asp Glu Gln Leu Lys Ser
            115                 120                 125

Gly Thr Ala Ser Val Val Cys Leu Leu Asn Asn Phe Tyr Pro Arg Glu
130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
                180                 185                 190

Tyr Ala Cys Glu Val Thr His Gln Gly Leu Ser Ser Pro Val Thr Lys
            195                 200                 205

Ser Phe Asn Arg Gly Glu Cys
    210                 215

<210> SEQ ID NO 23
<211> LENGTH: 427
<212> TYPE: PRT
<213> ORGANISM: Artificial Sequence
<220> FEATURE:
<223> OTHER INFORMATION: Synthetic Polypeptide

<400> SEQUENCE: 23

Met Glu Val Gln Leu Val Glu Ser Gly Gly Gly Leu Val Gln Pro Gly
1               5                   10                  15

Gly Ser Leu Arg Leu Ser Cys Ala Ala Ser Gly Phe Asn Ile Lys Asp
                20                  25                  30

Thr Tyr Ile His Trp Val Arg Gln Ala Pro Gly Lys Gly Leu Glu Trp
            35                  40                  45

Val Ala Arg Ile Tyr Pro Thr Asn Gly Tyr Thr Arg Tyr Ala Asp Ser
        50                  55                  60

Val Lys Gly Arg Phe Thr Ile Ser Ala Asp Thr Ser Lys Asn Thr Ala
65                  70                  75                  80

Tyr Leu Gln Met Asn Ser Leu Arg Ala Glu Asp Thr Ala Val Tyr Tyr
                85                  90                  95

Cys Ser Arg Trp Gly Gly Asp Gly Phe Tyr Ala Met Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
```

-continued

```
              210                 215                 220
Glu Ala Ala Ala Lys Glu Ala Ala Lys Asp Lys Asp Cys Glu Met
225                 230                 235                 240

Lys Arg Thr Thr Leu Asp Ser Pro Leu Gly Lys Leu Glu Leu Ser Gly
                245                 250                 255

Cys Glu Gln Gly Leu His Glu Ile Ile Phe Leu Gly Lys Gly Thr Ser
                260                 265                 270

Ala Ala Asp Ala Val Glu Val Pro Ala Pro Ala Ala Val Leu Gly Gly
                275                 280                 285

Pro Glu Pro Leu Met Gln Ala Thr Ala Trp Leu Asn Ala Tyr Phe His
                290                 295                 300

Gln Pro Glu Ala Ile Glu Glu Phe Pro Val Pro Ala Leu His His Pro
305                 310                 315                 320

Val Phe Gln Gln Glu Ser Phe Thr Arg Gln Val Leu Trp Lys Leu Leu
                325                 330                 335

Lys Val Val Lys Phe Gly Glu Val Ile Ser Tyr Ser His Leu Ala Ala
                340                 345                 350

Leu Ala Gly Asn Pro Ala Ala Thr Ala Ala Val Lys Thr Ala Leu Ser
                355                 360                 365

Gly Asn Pro Val Pro Ile Leu Ile Pro Cys His Arg Val Val Gln Gly
                370                 375                 380

Asp Leu Asp Val Gly Gly Tyr Glu Gly Gly Leu Ala Val Lys Glu Trp
385                 390                 395                 400

Leu Leu Ala His Glu Gly His Arg Leu Gly Lys Pro Gly Leu Gly Leu
                405                 410                 415

Val Pro Arg Gly Ser His His His His His His
                420                 425
```